(12) United States Patent
Krieger et al.

(10) Patent No.: US 7,078,511 B1
(45) Date of Patent: Jul. 18, 2006

(54) CLASS BI AND CI SCAVENGER RECEPTORS

(75) Inventors: Monty Krieger, Needham, MA (US); Susan L. Acton, Somerville, MA (US)

(73) Assignee: Massachusette Institute of Technology, Cambridge, MA (US)

( * ) Notice: Subject to any disclaimer, the term of this patent is extended or adjusted under 35 U.S.C. 154(b) by 621 days.

(21) Appl. No.: 08/765,108

(22) PCT Filed: Jun. 19, 1995

(86) PCT No.: PCT/US95/07721

§ 371 (c)(1),
(2), (4) Date: Mar. 27, 1997

(87) PCT Pub. No.: WO96/00288

PCT Pub. Date: Jan. 4, 1996

Related U.S. Application Data

(63) Continuation-in-part of application No. 08/265,428, filed on Jun. 23, 1994, now Pat. No. 6,429,289.

(51) Int. Cl.
| | |
|---|---|
| C07K 1/00 | (2006.01) |
| C07H 21/04 | (2006.01) |
| C12N 1/20 | (2006.01) |
| C12P 21/06 | (2006.01) |
| G01N 33/567 | (2006.01) |

(52) U.S. Cl. ..................... 536/23.5; 435/6; 435/7.21; 435/69.1; 435/252.3; 435/320.1; 436/501; 530/350; 514/2

(58) Field of Classification Search ............ 435/6, 435/7.1, 7.2, 69.1, 252.3, 320.1; 536/23.5
See application file for complete search history.

(56) References Cited

U.S. PATENT DOCUMENTS

| | | | |
|---|---|---|---|
| 3,625,214 | A | 12/1971 | Higuchi |
| 4,244,946 | A | 1/1981 | Rivier et al. |
| 4,305,872 | A | 12/1981 | Johnston et al. |
| 4,316,891 | A | 2/1982 | Guillemin et al. |
| 4,629,784 | A | 12/1986 | Stammer |
| 4,789,734 | A | 12/1988 | Pierschbacher |
| 4,792,525 | A | 12/1988 | Ruoslahti et al. |
| 4,868,116 | A | 9/1989 | Morgan et al. |
| 4,906,474 | A | 3/1990 | Langer et al. |
| 4,925,673 | A | 5/1990 | Steiner et al. |
| 4,980,286 | A | 12/1990 | Morgan et al. |
| 5,998,141 | A * | 12/1999 | Acton |

FOREIGN PATENT DOCUMENTS

| | | |
|---|---|---|
| JP | 03 290184 | 12/1991 |
| JP | 05 192179 | 8/1993 |
| WO | WO 90/05748 | 5/1990 |
| WO | WO 93/01286 | 1/1993 |

OTHER PUBLICATIONS

Calvo et al., *J. Biol. Chem.* 268()25; 18929-18935, Sep. 5, 1993.*
Oquendo et al. "CD36 Directly Mediaes Cytoadherence of *Plasmodium falciparum* Parasitized Erythrocytes". *Cell* 58:95-101, Jul. 14, 1989.*
Cao, G., et al. *J. Biol. Chem.* 272(52)33068-33076, 1997.*
Degrave, W. et al., *Molec. Biol. Rep.* 11(57-61) 1986.*
Sambrook et al, 1989 *Molecular Cloning: A laboratory Manual*, pp. 9.5-9.6.*
The Protein Folding Problem and Teritary Structure Prediction (1993), Birkauser, Boston, pp. 492-495.*
Bowie et al., 1990, *Science* 247:1306-1310.*
De Rijke, et al., "Binding characteristics of scavenger receptors on liver endothelial and Kupffer cells for modified low-density lipoproteins," *Biochem. J.* 304:69-73 (1994).
Fukasawa, et al., "Chinese Hamster Ovary Cells Expressing Novel Type of Acetylated Low Density Lipoprotein Receptor," *J. of Biol. Chem.* 270(4):1921-1927 (1995).
Kobzik, "Lung Macrophage Uptake of Unopsonized Environmental Particles," *J. of Immunol.* 155(1):367-376 (1995).
Krieger, "Molecular Flypaper and atherosclerosis: structure of the macrophage scavenger receptor," *Trends Biochem. Sci.* 17:141-146 (1992).
Krieger, "Molecular Flypaper, Host Defense, and Atherosclerosis," *J. Biol. Chem.* 268(7):4569-4572 (1993).
Luoma, et al., "Expression of $\alpha_2$-Macroglobuil Receptor/Low Density Lipoprotein Receptor-related Protein and Scavenger Receptor in Human Atherosclerotic Lesions," *J. Clin. Inv.* 93(5):2014-2021 (1994).
Rigotti, et al., "The Class B Scavenger Receptors SR-BI and CD36 Are Receptors for Anionic Phospholipids," *J. Biol. Chem.* 270(27):16221-16224 (1995).
Sambrook, Fritsch, and Maniatis. *Molecular Cloning: A Laboratory Manual*, Second Edition, Cold Spring Harbor, NY, Cold Spring Harbor Laboratory Press (1989) (Table of Contents only).

(Continued)

*Primary Examiner*—Janet L. Andres
*Assistant Examiner*—Michael Brannock
(74) *Attorney, Agent, or Firm*—Pabst Patent Group LLP

(57) ABSTRACT

Two distinct scavenger receptor type proteins having high affinity for modified lipoproteins and other ligands have been isolated, characterized and cloned. HaSR-BI, an AcLDL and LDL binding scavenger receptor, which is distinct from the type I and type II macrophage scavenger receptors, has been isolated and characterized and DNA encoding the receptor cloned from a variant of Chinese Hamster Ovary Cells, designated Var-261. dSR-CI, a non-mammalian AcLDL binding scavenger receptor having high ligand affinity and broad specificity, was isolated from *Drosophila melanogaster*. The isolated receptors are useful in screening for drugs that inhibit uptake of cholesterol in endothelial or adipose cells or macrophages, respectively. They are also useful as probes for the isolation of other lipoprotein receptors and in research the roles of these receptors.

16 Claims, 11 Drawing Sheets

OTHER PUBLICATIONS

Swida, et al., "Glue protein genes in *Drosophila virilis*: their organization, developmental control of transccription and specific mRNA degradation," *Development* 108(2):269-280 (1990).

Abrams, et al., "Macrophages in *Drosophila* embryos and L2 cells exhibit scavenger receptor-mediated endocytosis," *Proc. Natl. Acad. USA* 89:10375-10379 (1993).

Abumrad, et al., "Cloning of a Rat Adipocyte Membrane Protein Implicated in Binding or Transport of Long-chain Fatty Acids that is induced during Preadipocyte Diffrentiation," *J. Biol. Chem.* 268:17665-17668 (1993).

Acton, et al., "Expression Cloning of SR-BI, a CD36-related Class B Scavenger Receptor," *J. Biol. Chem.* 269(33):21003-21009 (1994).

Acton, et al., "The Collagenous Domains of Macrophage Scavenger Receptors and Complement Component C1g Mediate Their Similar, But Not Identical, Binding Specificities for Polyanionic Ligands," *J. Biol. Chem.* 268:3530-3537 (1993).

Agrawal, et al., "Oligodeoxynucleoside phosphoramidates and phosphorothioates as inhibitors of human immunodeficiency vurus," *Proc. Natl. Acad. Sci. USA* 85:7079-7083 (1988).

Arai, et al., "Multiple Receptors for Modified Low Density Lipoproteins in Mouse Peritoneal Macrophages: Different Uptake Mechanisms for Acetylated and Oxidized Low Density Lipoproteins," *Biochem. Biophys. Res. Commun.* 159:1375-1382 (1989).

Aruffo, et al., "Molecular cloning of a CD28 cDNA by a high-efficiency COS cell expression system," *Immunology* 84:8573-8577 (1987).

Asch, et al., "Isolation of the Thrombospondim Membrane Receptor," *J. Clin. Invest.* 79:1054-1061 (1987).

Ashkenas, et al., "Structures and high and low affinity ligand binding properties of murine type I and type II macrophage scavenger receptors," *J. Lipid Res.* 34:983-1000 (1993).

Askew, et al., "Molecular Recognition with Convergent Functional Groups, Synthetic and Structural Studies with a Model Receptor for Nucleic Acid Components," *J. Am. Chem. Soc.* 111:1082-1090 (1989).

Baldini, et al., "Cloning of a Rab3 isotype predominately expressed in adipocytes," *Proc. Natl. Acad. Sci. USA* 89:5049-5052 (1992).

Basu, et al., "Independent Pathways for Secretion of Cholesterol and Apolipoprotein E by Macrophages," *Science* 219:871-873 (1983).

Bickel, et al., "Rabbit Aortic Smooth Muscle Cells Express Inducible Scavenger Receptor Messenger RNA That is Absent from Endothelial Cells," *J. Clin. Invest.* 90:1450-1457 (1992).

Blume, et al., "Triple helix by purine-rich oligonucleotides targeted to the human dihydrofolate rductase promoter," *Nucl. Acids Res.* 20:1777-1784 (1992).

Brown, et al., "Lipoprotein Metabolism in the Macrophage: Implications for Cholesterol Deposition in Atherosclerosis," *Annu. Rev. Biochem.* 52:223-261 (1983).

Calvo, et al., "Identification, Primary Structure, and Distribution of CLA-1, a Novel Member of the CD36/LIMPHII Gene Family," *J. Biol. Chem.* 268 (25):18929-18935 (1993).

Charron, et al., "A glucose transport protein expressed predominately in insulin-responsive tissues," *Proc. Natl. Acad. Sci USA* 86:2535-2539 (1989).

Chen, et al., "NPXY, a Sequence Often Found in Chyoplasmic Tails, is Required for Coated Pit-mediated Internalization of the Low Density Lipoprotein Receptor," *J. Clin. Chem.* 265:3116-3123 (1990).

Clackson, T., et al., "Making antibody fragments using phage display libraries," *Nature* 352:624-688 (1991).

Cooney, et al., "Site-Specific Oligonucleotide Binding Represses Transcription of the Human *c-myc* Gene In Vitro," *Science* 241, 456-459 (1988).

Crooke, "Progress toward oligonucleotide therapeutics: pharmacodynamic properties," *FASEB J.* 7:533-539 (1993).

Cullen, "Use of Eukaryotic Expression Technology in the Functional Analysis of Cloned Genes," *Methods in Enz.* 152:684-704 (1987).

Daugherty, et al., "Polymerase chain reaction facilitates the cloning, CDR-grafting and rapid expression of a murine monoclonal antibody directed against the CD18 component of leukocyte integrins," *Nucl. Acids Res.* 19:2471-2476 (1991).

Doi, et al., "Charged Collagen Structure Mediates the Recognition of Negativity Charged Macromolecules by Macrophage Scavenger Receptors," *J. Clin. Chem.* 268:2126-2133 (1993).

Duval-Valentin, et al., "Specific inhibition of transcription by triple helix-forming oligonucleotides," *Proc. Natl. Acad. Sci. USA* 89:504-508 (1992).

Ellington, et al., "Selection *in vitro* of singles-stranded DNA molecules that fold into specific ligand-binding structures," *Nature* 355:850-852 (1992).

Endemamn, et al., "CD36 is a Receptor for Oxidized Low Density Lipoprotein," *J. Biol. Chem.* 268:11811-11816 (1993).

Faust, et al., "Expression of Specific High Capacity Meyalonate Transport in a Chinese Hamster Ovary Cell Variant," *J. Biol. Chem.* 262:1996-2004 (1987).

Fraser, et al., "Divalent cation-independent macrophage adhesion inhibited by monoclonal antibody to murine scavenger receptor," *Nature* 364:343-346 (1993).

Freeman, et al., "Expression of type I and type II bovine scavenger receptors in Chinese hamster ovary cells: Lipid droplet accumulation and nonreciprocal cross competition by acetylated and oxidized low density lipoprotein," *Proc. Natl. Acad. Sci. USA* 88:4931-4935 (1991).

Goldstein, et al., "Binding site on macrophages that mediates uptake and degradation of acetylated low density lipoprotein, producing massive cholesterol deposition," *Proc. Natl. Acad. Sci. USA* 76:333-337 (1979).

Goldstein, et al., "Receptor-Mediated Endocytosis of Low-Density Lipoprotein in Cultured Cells," *Methods Enzymol.* 98:241-260 (1993).

Greenwalt, et al., "Membrane Glycoprotein CD36: A Review of Its Roles in Adherence, Signal Transduction, and Transfusion Medicine," *Blood* 80:1105-1115 (1992).

Gregoriadis, G., Chapter 14. "Liposomes",*Drug Carriers in Biology and Medicine* pp. 287-341 (Academic Press, 1979).

Grigoriev, et al., "A Triple Helix-forming Oligonucleotide-Intercalator Conjugate Acts as a Transcriptional Repressor via inhibition of NF $_k$B Binding of Interleukin-2 Receptor $_\alpha$-Regulatory Sequence," *J. Biol. Chem.* 267:3389-3395 (1992).

Haberland, et al., "Role of the Maleyl-Albunim Receptor in Activation of Murine Peritoneal Macrophages In Vitro," *J. Immunol.* 142:855-862 (1989).

Haberland, et al., "Two Distinct Receptors Account for Recognition of Maleyl-Albunim in Human Monocytes During Differentiation In Vitro," *J. Clin. Inves.* 77:681-689 (1986).

Hart, et al., "A *Drosophila* Gene Encoding an Epithelial Membrane Protein with Homology to CD36/LIMP II," *J. Mol. Biol.* 234:249-253 (1993).

Herz, et al., "Surface location and high affinity for calcium of a 500-kd liver membrane protein closely related to the LDL-receptor suggest a physiological role as lipoprotein receptor," *EMBO J.* 4119-4127 (1988).

Holt, et al., "An Oligomer Complementary to *c-myc* mRNA Inhibits Proliferation of HL-60 Promyelocytic Cells and Induces Differentiation," *Mol. Cell. Biol.* 8:963-973 (1988).

Horiuchi, et al., "Scavebger Function if Sinusoidal Liver Cells: Acetylated Low-density Lipoprotein is Endocytosed via a Route Distinct from Formaldehyde-treated Serum Albumin." *J. Biol. Chem.* 259:53-56 (1985).

Huang, et al., "Membrane glycoprotein IV (CD36) is physically associated with the FYN, Lyn, and Yes protein-tyrosine kinases in human platelets," *Proc. Natl. Acad. Sci. USA* 88(17):7844-7848 (1991).

Hunt, et al., "Characterization and sequence of a mouse hsp70 gene and its expression in mouse cell lines," *Gene* 87:199-204 (1990).

Inaba, et al., "Macrophage Colony-stimulating Factor Regulates Both Activities of Neural and Acidic Cholesteryl Ester Hydrolses in Human Monocyte-derived Macrophages," *J. Clin. Invest.* 92(2):750-757 (1993).

Itakura et al., "Synthesis and use of synthetic oligonucleotides," *Ann. Rev. Biochem.* 53:323-356 (1984).

Kabat, et al., Sequences of Proteins of Immunological Interest, 4th Ed. (U.S. Dept. Health and Human Services, Bethesda, MD, 1987).

Kingsley, et al., "DNA-Mediated Transfer of a Human Gene Required for Low-Density Lipoprotein Receptor Expression and for Multple Golgi Processing Pathways," *Mol. Cell. Biol.* 6:2734-2737 (1986).

Kingsley, et al., "Receptor-mediated endocytosis of low density lipoprotein: Somatic cell mutants define multiple genes required for express of surface-receptor activity," *Proc. Natl. Acad. Sci. USA* 81:5454-5458 (1984).

Kodama, et al., "Type I macrophage scavenger receptor contains $\alpha$-helical and collagen-like coiled coils," *Nature* 343:531-535 (1990).

Krieger, "Contemplation of Mutations in the LDL Pathways of Receptor-Mediated Endocytosis by Cocultivation of LDL Receptor-Defective Hamster Cell Mutants," *Cell* 33:413-422 (1983).

Krieger, "Reconstitution of the Hydrophobic Core of Low-Density Lipoprotein," *Meth. Enzymol.* 128:608-613 (1986).

Krieger, et al., "Amphotericin B selection of mutant Chinese hamster cells eith defects in the receptor-mediated endocytosis of low density lipoprotein and cholesterol and cholesterol biosynthesis," *Proc. Natl. Acad. Sci. USA* 80:5607-5611 (1983).

Krieger, et al., "Isolation of Chimese Hamster Cell Mutants Defective in the Receptor-mediated Endocytosis of Low Density Lipoprotein," *J. Mol. Biol.* 150:167-184 (1981).

Krieger, et al., "Reconstituted Low Density Lipopsrotein," *J. Supra. Struct.* 10:467-478 (1979).

Krieger, et al., "Structures and Functions of Multiligand Lipoprotein Receptors: Macrophage Scavenger receptors and LDL Receptor-Related Protein (LRP)," *J. Annu. Rev. Biochem.* 63:601-637 (1994).

Krieger, et al., *Cold Spring Harbor symposia on Quantitative Biology* vol. LVII. 605-609 (1992).

Lewis, et al., "Automated site directed drug design: the concept of spacer skeletons for primary structure generation," *Proc. R. Soc. Lond.* 236, 125-140 and 141-163 (1989).

Lowry, et al., "Protein Measurement with the Folin Phenol Reagent," *J. Biol. Chem.* 193:265-275 (1951).

Maher, et al., "Inhibition of DNA Binding Proteins by Oligonucleotide-Directed Triple Helix Formation," *Science* 245:725-730 (1989).

Matsumoto, et al., "Human macrophage scavenger receptors: Primary structure expression, and localization in atherosclerotic lesions," *Proc. Natl. Acad. Sci. USA* 87:9133-9137 (1990).

McKinaly, et al., "Rational design of antiviral agents," *Annu. Rev. Pharmacol. Toxicol,* 29:111-122 (1989).

Merrifield, "solid Phase Peptide Synthesis I. The Synthesis of a Tetrapeptide," *J. Am. Chem. Soc.* 85:2149-2154 (1964).

Moestrup, et al., Distribution of the $\alpha_2$-macroglobulin receptor/low density lipoprotein receptor-related protein in human tissues, *Cell Tissue Res.* 269:375-382 (1992).

Mulligan, "The Basic Science of Gene Therapy," *Science* 260:926-932 (1993).

Nagelkerke, et al., "In Vivo and In Vitro Uptake and Degradation of Acetylated Low Density Lipoprotein by Rat Liver Endothelial, Kupffer, and Parenchymal Cells," *J. Biol. Chem.* 258:12221-12227 (1983).

Naito, et al., "Tissue Distribution Intracellular Localization, and In Vitro Expression of Bovine Macrophage Scavenger Receptors," *Am. J. Pathol.* 139:1411-1423 (1991).

Narang, et al., in "Chemical Synthesis of Deoxyoligonucleotides by the Modified Triestser Method," *Methods Enzymol.* 65:610-620 (1980).

Ockenhouse, et al., Activation of Monocytes and Platelets by Monoclonal Antibodies or Malaria-infected Erythrocytes Binding to the CD36 Surface Receptor in vitro, *J. Clin. Invest.* 84:468-475 (1989).

Offensperger, et. al., "In vivo inhibition of duck hepatitis B virus replication and gene expression by phosphorothioate modified antisense oligodeoxynucleotides," *EMBO J.* 12:1257-1262 (1993).

Oquendo, et al., "CD36 Directly Mediates Cytoadherence of Plasmodium falciparium Parasitized Erythrocites," *Cell* 58:95-101 (1989).

Orson, et al., "Oligonucleotide inhibition of IL2R$\alpha$ mRNA transcriptionby promoter region collinear triplex formation in lymphocytes," *nucl. Acids Res.* 19:3435-3441 (1991).

Ottnad, et al., "Differation of binding sites on reconstituted hepatic scavenger receptors using oxidized low-density lipoprotein," *Biochem J.* 281:745-751 (1992).

Pearson, et al., "Expression cloning of Dsr-CI, a class C macrophage-specific scavenger receptor from *Drosphila melanogaster*," *Proc. Natl. Acaad. Sci. USA* 92:4056-4060 (1995).

Penman, et al., The Type I and Type II Bovine Scavenger Receptors Expressed in Chinese Hamster Ovary Cells are Trimeric Proteins with Collagenoous Triple Helical Domains Comprising Noncovalently Associated Monomers and $Cys^{83}$-Disulfide-linked Dimers, *J. Biol. Chem.* 266:23985-23993 (1991).

Perry, et al., "The Use of 3D Modeling Databases for Identifying Structure Activity Relationships," *QSAR: Quantitative Structure Activity Relationships in Drug Design* pp. 189-193 (Alan R. Liss, Inc. 1989).

Pitas, et al., "Uptake of Chemically Modified Low Density Lipoproteins In Vivo Is Mediated by Specific Endothelial Cells," *J. Cell. Biol.* 100:103-117 (1985).

Postel, et al., "Evidence that a triplex-forming oligodeoxyribonucleotide binds to the c-myc promoter in HeLa cells, thereby reducing *c-myc* mRNA levels," *Proc. Natl. Acad. Sci. USA* 88:8227-8231 (1991).

Predescu, et al., "Binding and Transcytosis of Glycoalbunim by the Microvascular Endothelium of the Nature Myocardium: Evidence that Glycoalbumin Behaves as a Bifunctional Ligand," *J. Cell Biol.* 107:1729-1738 (1988).

Ripka, "Computers picture the perfect drug," *New Scientist* 54-57 (Jun. 16, 1988).

Rohrer, et al., "Coiled-coil fibrous domains mediate ligand binding by macrophage scavenger receptor type II," *Nature* 343:570-572 (1990).

Rouvinen, et al., "Computer-aided Drug Design," *Acta Pharmaceutica Fennica* 97:159-166 (1988).

Sarin et al., "Inhibition of acquired immunodeficiency syndrome virus by oligodeoxynucleoside methylphosphonates," *Proc. Natl. Acad. Sci. USA* 85:7448-7451 (1989).

Savill, et al., "Macrophage Vitronectin Receptor CD36 and Thrombospondin Cooperate in Recognition of Neutrophilis Undergoing Programmed Cell Death," *Chest* 99:6S-7S (suppl) (1991).

Schaub, et al., "Recombinant Human Macrophage Colony-Stimulating Factor Reduces Plasma Cholesterol and Carrageenee Granuloma Foam Cell Formation in Watanabe Heritable Hyperlipidemic Rabbits," *Arterioscler. Thromb.* 14(1):70-76 (1994).

Schnitzer, et al., "Preferential Interaction of Albumin-binding Proteins, gp30 and gp18, with Conformationally Modified Albumins,"*J. Biol. Chem.* 267:24544-24553 (1992).

Scriver, et al., Eds., in *The Metabolic and Molecular Bases of Inherited Disease*, vol. 11, 7th Ed., pp. 2033; 2060-2061, New York, McGraw Hill.

Sege, et al., "Characterization of a Family of Gamma-Ray-Induced CHO Mutants Demonstrates that the IdlA Locus is Diploid and Encodes the Low-Density Lipoprotein Receptor,"*Mol. Cell. Biol.* 6:3268-3277 (1986).

Sege, et al., "Expression and regul;ation of human low-density lipoprotein receptors in Chinese hamster ovary cells," *Nature* 307:742-745 (1984).

Shaw, et al., "Modified deoxyoligonucleotides stable to exonuclease degradation in serum," *Nucleic Acids Res.* 19:747-750 (1991).

Sparrow, et al., "A Macrophage Receptor That Recognizes Oxidized Low Density Lipoprotein but Not Acetylated Low Density Lipoprotein," *J. Biol. Chem.* 264:2599-2604 (1989).

Stanton, et al., "A Macrophage Fe Receptor for IgG Is Also a Receptor for Oxidized Low Density Lipoprotein," *J. Biol. Chem.* 267:22446-22451 (1992).

Steinberg, et al., "Beyond Cholesterol: Modifications of Low-Density Lipoprotein That Increase Its Atherogenicity," *N. Engl. J. Med.* 320:915-924 (1989).

Stent, G.S., et al., *Molecular Genetics*, pp. 213-219 (1971).

Szostak, "In Vitro Genetics," *TIBS* 19:89-93 (1992).

Tandon, et al., "Identification of Glycoprotein IV (CD36) as a Primary Receptor for Platelet-Collagen Adhesion," *J. Biol. Chem.* 264:7576-7583 (1989).

Vandepol, et al., "Clinical Applications of Recombinant Macrophage-Colony Stimulating Factor (rhM-CSF)," *Biotech Therap.* 2:231-239 (1991).

Vega, et al., "Cloning Sequences and Expression of a cDNA Encoding Rat LIMP II, a Novel 74-kDa Lysosomal Membrane Protein Related to the Surface Adhesion Protein CD36," *J. Biol. Chem.* 266:16818-16824 (1991).

Via, et al., "Identification and density dependent regulation of the AC-LDL Receptor in normal and transformed bovine aortic endothelial cells (BAEC)," *The FASEB J.* 6:A371, #2135 (1992).

Villaschi, et al., "Binding and Uptake of Native amd Glcosylated Albumin-Gold Complexes in Perfused Rat Lungs," *Microvasc. Res.* 32:190-199 (1986).

Wickstrom, et al., "Human promyelocytic leukemia HL-60 cell proliferation and *c-myc* protein expression are inhibited by an antisense pentadecadeoxynucleotide targeted against *c-myc* mRNA," *Proc. Natl. Acad. Sci. USA* 85:1028-1032 (1988).

Young, et al., "Triple helix formation inhibits transcription elongation in vitro," *Proc. Natl. Acad. Sci. USA* 88:10023-10026 (1991).

Zamecnik, et al., "Inhibition of replication and expression of human T-cell lymphotropic virus type III in cultured cells by exogenous systhenic oligonucleotides complementary to viral RNA," *Proc. Natl. Acad. Sci.* 83:4143-4146 (1986).

Zamecnik, et al., "Inhibition of Rous sarcoma virus replication and cell transformation by a specific oligodeoxynucleotide," *Proc. Natl. Acad. Sci. USA* 75:280-284 (1978).

Zhu, et al., "Systemic Gene Expression AFter Intravenous DNA Delivery into Adult Mice," *Science* 261:209-211 (1993).

\* cited by examiner

CLASS BI AND CI SCAVENGER RECEPTORS

This application is a continuation-in-part of U.S. patent application Ser. No. 08/265,428 "Class BI and Class CI Scavenger Receptors" filed Jun. 23, 1994, now U.S. Pat. No. 6,429,289 by Monty Krieger, Susan L. Acton, and Alan M. Pearson.

BACKGROUND OF THE INVENTION

The present invention is generally in the area of new scavenger receptor proteins present on cells which can mediate lipid or lipoprotein uptake, genes encoding these proteins and methods of detection and use thereof.

The intercellular transport of lipids through the circulatory system requires the packaging of these hydrophobic molecules into water-soluble carriers, called lipoproteins, and the regulated targeting of these lipoproteins to appropriate tissues by receptor-mediated endocytic pathways. The most well characterized lipoprotein receptor is the LDL receptor, which binds to apolipoproteins B-100 (apoB-100) and E (apoE), which are constituents of low density lipoprotein, the principal cholesteryl-ester transporter in human plasma (LDL), very low-density lipoprotein, a triglyceride-rich carrier synthesized by the liver (VLDL), intermediate-density lipoprotein (IDL), and catabolized chylomicrons (dietary triglyceride-rich carriers synthesized by the liver).

All members of the LDL receptor gene family consist of the same basic structural motifs, shown in FIG. 1a. Ligand-binding (complement-type) cysteine-rich repeats of approximately 40 amino acids are arranged in clusters (ligand-binding domains) that contain between two and eleven repeats. Ligand-binding domains are always followed by EGF-precursor homologous domains. In these domains, two EGF-like repeats are separated from a third EGF-repeat by a spacer region containing the YWTD motif. In LRP and gp330, EGF-precursor homologous domains are either followed by another ligand-binding domain or by a spacer region. The EGF-precursor homology domain, which precedes the plasma membrane, is separated from the single membrane-spanning segment either by an O-linked sugar domain (in the LDL receptor and VLDL receptor) or by one (in C. elegans and gp330) or six EGF-repeats (in LRP). The cytoplasmic tails contain between one and three "NPXY" internalization signals required for clustering of the receptors in coated pits. In a later compartment of the secretory pathway, LRP is cleaved within the eighth EGF-precursor homology domain. The two subunits LRP-515 and LRP-85 (indicated by the brackets) remain tightly and non-covalently associated. Only partial amino acid sequence of the vitellogenin receptor and of gp330 are available.

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors type I and type II.

Scavenger receptors mediate the endocytosis of chemically modified lipoproteins, such as acetylated LDL (AcLDL) and oxidized LDL (OxLDL), and have been implicated in the pathogenesis of atherosclerosis (Krieger and Herz, 1994 J. Annu. Rev. Biochem. 63, 601–637; Brown and Goldstein, 1983 Annu. Rev. Biochem. 52, 223–261; Steinberg et al., 1989 N. Engl. J. Med. 320, 915–924).

Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 Proc. Natl. Acad. Sci. U.S.A. 88, 4931–4935, Krieger and Herz, 1994). Several investigators have suggested that there may be at least three different classes of such receptors expressed on mammalian macrophages, shown in FIG. 3, including receptors which recognize either AcLDL or OxLDL, or both of these ligands (Sparrow et al., 1989 J. Biol. Chem. 264, 2599–2604; Arai et al., 1989 Biochem. Biophys. Res. Commun. 159, 1375–1382; Nagelkerke et al., 1983 J. Biol. Chem. 258, 12221–12227).

The first macrophage scavenger receptors to be purified and cloned were the mammalian type I and II receptors. These are trimeric integral membrane glycoproteins whose extracellular domains have been predicted to include α-helical coiled-coil, collagenous and globular structures (Kodama et al., 1990 Nature 343, 531–535; Rohrer et al., 1990; Krieger and Herz, 1994). The collagenous domain, shared by the type I and type II receptors, apparently mediates the binding of polyanionic ligands (Acton et al., 1993 J. Biol. Chem. 268, 3530–3537; Doi et al., 1993 J. Biol. Chem. 268, 2126–2133). The type I and type II molecules, which are the products of alternative splicing of a single gene, are hereafter designated class A scavenger receptors (SR-AI and SR-AII). The class A receptors, which bind both AcLDL and OxLDL (Freeman et al., 1991), have been proposed to be involved in host defense and cell adhesion, as well as atherogenesis (Freeman et al., 1991; Krieger, 1992 Trends Biochem. Sci. 17, 141–146; Fraser et al., 1993 Nature 364, 343–346; Krieger and Herz, 1994).

Models of the predicted quaternary structures of the type I and type II macrophage scavenger receptors are shown in FIG. 1B (AR-A, I, II & III). Both contain six domains, of which the first five are identical: the N-terminal cytoplasmic region, the transmembrane region, spacer, α-helical coil, and collagen-like domains. The C-terminal sixth domain of the type I receptor is composed of an eight-residue spacer followed by a 102-amino acid cysteine-rich domain (SRCR), while the sixth domain of the type II receptor is only a short oligopeptide.

Using a murine macrophage cDNA library and a COS cell expression cloning technique, Endemann, Stanton and colleagues, (Endemann, et al. 1993 J. Biol. Chem. 268, 11811–11816; Stanton, et al. J. Biol. Chem. 267, 22446–22451), reported the cloning of cDNAs encoding two additional proteins that can bind OxLDL. The binding of OxLDL to these proteins was not inhibited by AcLDL. These proteins are FcgRII-B2 (an Fc receptor) (Stanton et al., 1992) and CD36 (Endemann et al., 1993). The significance of the binding of OxLDL to FcgRII-B2 in transfected COS cells is unclear because FcgRII-B2 in macrophages apparently does not contribute significantly to OxLDL binding (Stanton et al., 1992). However, CD36 may play a quantitatively significant role in OxLDL binding by macrophages (Endemann et al., 1993). In addition to binding oxidized LDL, CD36 binds thrombospondin (Asch et al., 1987 J. Clin. Invest. 79, 1054–1061), collagen (Tandon et al., 1989 J. Biol. Chem. 264, 7576–7583), long-chain fatty acids (Abumrad et al., 1993 J. Biol. Chem. 268, 17665–17668) and Plasmodium falciparum infected erythrocytes (Oquendo et al., 1989 Cell 58, 95–101). CD36 is expressed in a variety of tissues, including adipose, and in macrophages, epithelial cells, monocytes, endothelial cells, platelets, and a wide variety of cultured lines (Abumrad et al., 1993; and see Greenwalt et al., 1992 *Blood* 80, 1105–1115 for review). Although the physiologic functions of CD36 are not known, it may serve as an adhesion molecule due to its collagen-binding properties. It is also been proposed to be a long-chain fatty acid transporter (Abumrad et al., 1993) and a signal transduction molecule (Ockenhouse et al., 1989 *J. Clin. Invest.* 84, 468–475; Huang et al., 1991), and may serve as a receptor on macrophages for senescent neutrophils (Savill et al., 1991 *Chest* 99, 7 (suppl)).

Modified lipoprotein scavenger receptor activity has also been observed in endothelial cells (Arai et al., 1989; Nagelkerke et al., 1983; Brown and Goldstein, 1983; Goldstein et al., 1979 *Proc. Natl. Acad. Sci. U.S.A.* 76, 333–337). The endothelial cell activity apparently is not mediated by the class A scavenger receptors (Bickel et al., 1992 *J. Clin. Invest.* 90, 1450–1457; Arai et al., 1989; Nagelkerke et al., 1983; Via et al., 1992 *The Faseb J.* 6, A371), which are expressed almost exclusively by macrophages (Naito et al., 1991 *Am. J. Pathol.* 139, 1411–1423; Krieger and Herz, 1994). In vivo and in vitro studies suggest that there may be scavenger receptor genes expressed in endothelial cells and macrophages which differ from both the class A scavenger receptors and CD36 (Haberland et al., 1986 *J. Clin. Inves.* 77, 681–689; Via et al., 1992; Sparrow et al., 1989; Horiuchi et al., 1985 *J. Biol. Chem.* 259, 53–56; Arai et al., 1989; and see below). Via, Dressel and colleagues (Ottnad et al., 1992 *Biochem J.* 281, 745–751) and Schnitzer et al. 1992 *J. Biol. Chem.* 267, 24544–24553) have detected scavenger receptor-like binding by relatively small membrane associated proteins of 15–86 kD. In addition, the LDL receptor related protein (LRP) has been shown to bind lipoprotein remnant particles and a wide variety of other macromolecules. Both the mRNA encoding LRP and the LRP protein are found in many tissues and cell types (Herz, et al., 1988 *EMBO J.* 7:4119–4127; Moestrup, et al., 1992 *Cell Tissue Res.* 269: 375–382), primarily the liver, the brain and the placenta. The predicted protein sequence of the LRP, shown in FIG. 1A, consists of a series of distinctive domains or structural motifs, which are also found in the LDL receptor.

Based on the information known regarding the structures and functions of multiligand lipoprotein receptors present on macrophages, it would clearly be of benefit to isolate and clone other members of the lipoprotein receptor family present on macrophages, especially from non-mammalian species, in order to investigate which aspects of these molecules are most conserved and which portions can therefore be selectively targeted for stimulation or inhibition of binding, and on other cell types, the structure and function of whose receptors are not characterized.

It is therefore an object of the present invention to provide the structure, amino acid sequence, and DNA sequence encoding a previously undescribed lipoprotein receptors present on mammalian cells.

It is another object of the present invention to provide the structure, amino acid sequence, and DNA sequence encoding a lipoprotein receptor present on insect macrophages.

It is a further object of the present invention to provide methods and reagents for use in isolating and characterizing lipoprotein receptors that are not type I and type II macrophage scavenger receptors nor classic LDL receptors.

It is yet a still further object of the present invention to provide methods and reagents for designing drugs that can stimulate or inhibit the binding of lipoprotein receptors that are not type I and type II macrophage scavenger receptors nor classic LDL receptors.

It is still another object of the present invention to provide a method and means for altering cholesterol uptake and transport by cells.

SUMMARY OF THE INVENTION

Two distinct scavenger receptor type proteins having high affinity for modified lipoproteins and other ligands have been isolated, characterized and cloned. HaSR-BI, an AcLDL and LDL binding scavenger receptor, which is distinct from the type I and type II macrophage scavenger receptors, has been isolated and characterized and DNA encoding the receptor cloned from a variant of Chinese Hamster Ovary Cells, designated Var-261, and from murine cells. dSR-CI, a non-mammalian AcLDL binding scavenger receptor having high ligand affinity and broad specificity, was isolated from *Drosophila melanogaster*.

It has been discovered that the SR-BI receptor is expressed principally in steroidogenic tissues and adrenal tissue and appears to mediate HDL-transfer and uptake of cholesterol. Competitive binding studies show that SR-BI binds LDL, modified LDL, negatively charged phospholipid, and HDL. Direct binding studies show that SR-BI binds HDL-lipid, without degradation of the HDL, and lipid is accumulated within cells expressing the receptor. These studies indicate that AR-BI plays a major role in transfer of cholesterol from the liver to the steroidogenic tissues, and that increased expression in the liver or other tissues may be useful in increasing uptake of cholesterol by cells expressing SR-BI, thereby decreasing levels in foam cells and deposition at sites involved in atherogenesis.

The presence of scavenger receptors on both mammalian and *Drosophila* macrophages indicates that they mediate critical, well-conserved functions, including pathogen recognition, and that they may have appeared early in the evolution of host defense systems. In this regard, it is known that postembryonic macrophage-like hemocytes in *Drosophila* participate in wound healing, encapsulation of pathogens, and phagocytosis. Due to the known association between atherosclerosis and macrophages, and the uptake of cholesterol by macrophages which is mediated by scavenger receptor proteins, the isolated receptors are useful in screening for drugs that inhibit uptake of cholesterol by cells expressing these receptors. Studies also demonstrate that a 600 bp BamHI portion of the cDNA encoding SR-BI hybridizes under stringent conditions to a mRNA expressed in adipocytes. The hybridizing sequence does not express a protein immunoreactive with antibody to SR-BI. The protein encoded by the hybridizing sequence is referred to as SR-BII.

BRIEF DESCRIPTION OF THE DRAWINGS

FIG. 2A is binding at 4° C.; FIG. 2B is binding plus uptake at 37° C.; and FIG. 2C is degradation at 37° C., measured as ng $^{125}$I-AcLDL/5 hr/mg cell protein versus $^{125}$I-AcLDL (μg protein/ml).

FIG. 6A is binding at 4° C.; FIG. 6B is binding plus uptake at 37° C.; and FIG. 6C is degradation at 37° C., measured as ng $^{125}$I-AcLDL/5 hr/mg cell protein versus $^{125}$I-AcLDL (µg protein/ml).

DETAILED DESCRIPTION OF THE INVENTION

Figure 1A:
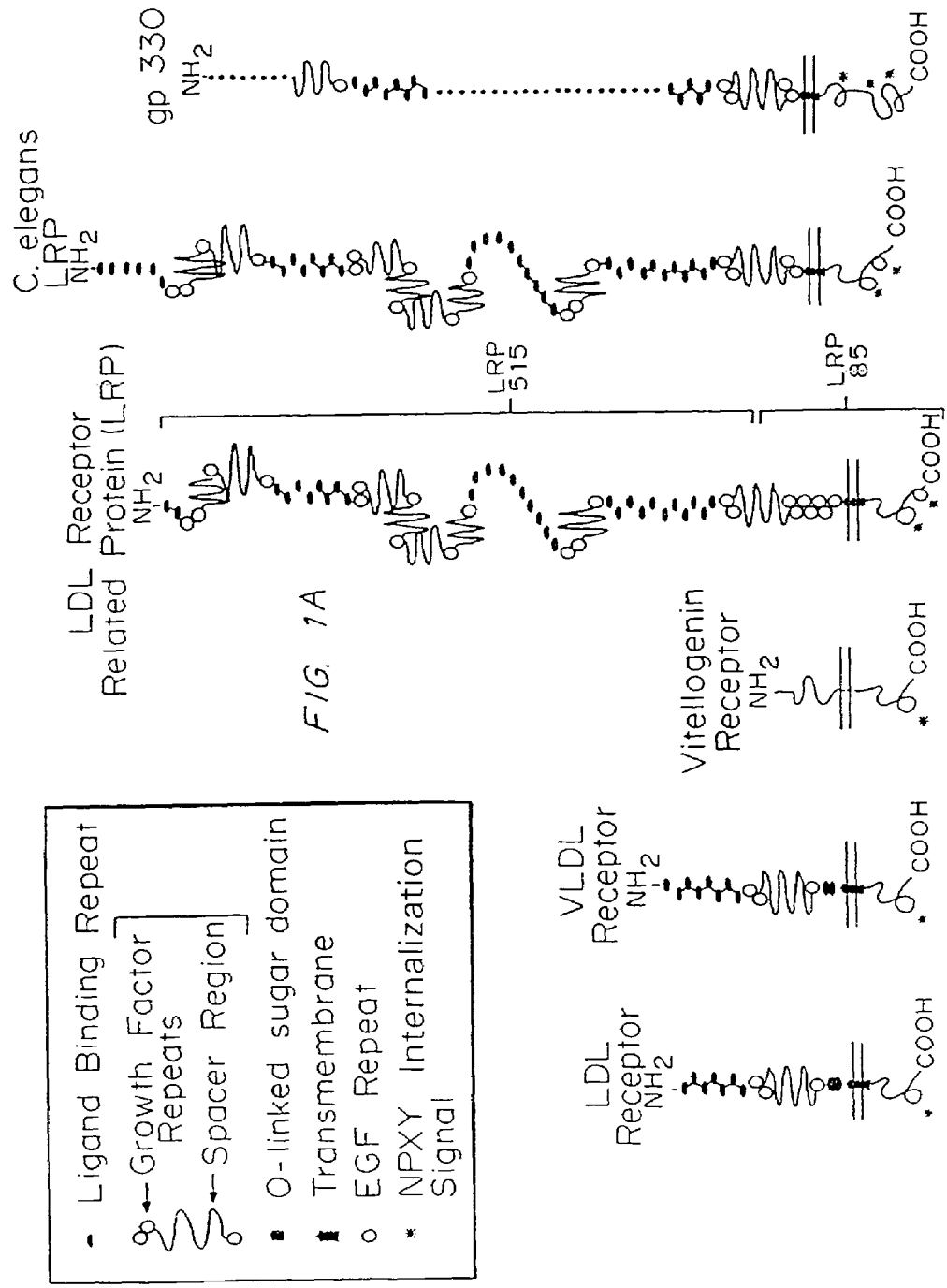
FIG. 1*a* is a schematic of the LDL receptors described in the background of the invention.

In order to isolate, characterize, and clone the genes for new scavenger receptors and other lipoprotein receptors, cDNA and genomic libraries are prepared from cells in which activities have been identified which are characteristic of scavenger receptors: binding to lipoproteins such as LDL, HDL, AcLDL and/or oxidized-LDL; hybridization screening of the genomic libraries using probes generated from the nucleic acid sequences of cloned receptors; expression cloning by transient expression in COS cells and/or expression cloning by stable expression in CHO cells; analysis of the cloned cDNA: verification, sequencing and sequence analysis; identification and isolation of the genomic DNA including regulatory sequences; immunochemical analysis of the structure and biosynthesis of the new scavenger receptors; and characterization of the binding properties of the new receptors and comparisons with type I and type II receptors.

I. Isolation and Characterization of a Mammalian Scavenger Receptor Protein on CHO Cells.

To extend the analysis of the structure and function of mammalian modified lipoprotein scavenger receptors, a variant Chinese hamster ovary cell line, Var-261, which, based on ligand specificity, expresses an apparently novel polyanion binding scavenger receptor, was identified and characterized. The cDNA for a scavenger receptor, haSR-BI, which is a new member of the CD36 family of membrane proteins (class B scavenger receptors), was isolated from the Var-261 cells. Although isolated from the same cells, haSR-BI is not responsible for the novel polyanion binding receptor activity of Var-261 cells, and is present in normal cells present in a variety of tissues, as discussed below.

The ligand specificities of CD36 and haSR-BI expressed in transfected cell lines was compared with that of Var-261 cells. haSR-BI differs from CD36 and other modified lipoprotein receptors described to date in that its binding of AcLDL is inhibited by native LDL. SR-BI also binds HDL and mediates uptake of lipid from HDL into the cell.

The cDNA encoding SR-BI yields a predicted protein sequence of 509 amino acids which is approximately 30% identical to those of the three previously identified CD36 family members. Northern blot analysis of murine tissues shows that SR-BI is most abundantly expressed in fat and is present at moderate levels in lung and liver. Furthermore, SR-BI mRNA expression is induced upon differentiation of 3T3-L1 cells into adipocytes. Both SR-BI and CD36 display high affinity binding for acetylated LDL with an apparent dissociation constant in the range of approximately 5 µg protein/ml. The ligand binding specificities of CD36 and SR-BI, determined by competition assays, are similar, but not identical: both bind modified proteins (acetylated LDL, maleylated BSA), but not the broad array of other polyanions (e.g. fucoidin, polyinosinic acid, polyguanosinic acid) which are ligands of the class A receptors. SR-BI displays high affinity and saturable binding of HDL which is not accompanied by cellular degradation of the HDL. HDL inhibits binding of AcLDL to CD36, suggesting that it binds HDL, similarly to SR-BI. Native LDL, which does not compete for the binding of acetylated LDL to either class A receptors, CD36 or Var-261 cells, unexpectedly competes for binding to SR-BI. SR-BI and CD36 therefore define a second class of scavenger receptors, designated class B, which are referred to as members of the CD36 family which can bind to modified LDL. The ability of other known members of the CD36 family to bind to modified LDLs has not been reported. Class B scavenger receptors may play a role in the in vivo and in vitro uptake of modified proteins previously described by Haberland et al., 1989 *J. Immunol.* 142, 855–862; Villaschi et al., 1986 *Microvasc. Res.* 32, 190–199; Horiuchi et al., 1985; Predescu et al., 1988 *J. Cell Biol.* 107, 1729–1738).

These methods and conclusions are described in greater detail below. Abbreviations: LDL (low density lipoprotein), OxLDL (oxidized LDL), AcLDL (acetylated LDL), M-BSA (maleylated BSA), CHO (Chinese hamster ovary), haSR-BI (hamster scavenger receptor type BI), mSR-AII (murine scavenger receptor type AII), huCD36 (human CD36).

Materials and Methods

Materials

LDL, AcLDL, $^{125}$I-labeled AcLDL (100–400 cpm/ng protein), and newborn calf and human lipoprotein-deficient sera were prepared as described by Goldstein et al., 1983 *Methods Enzymol.* 98, 241–260; Krieger, 1983 *Cell* 33, 413–422. For some preparations of LDL and AcLDL, the following additional precautions were taken to prevent inadvertent oxidation: 1) 20 µM β-hydroxytoluene was added to the plasma before separation of the lipoproteins on the gradient, 2) one hour prior to all dialysis steps the dialysis solutions were degassed by vacuum, followed by purging with nitrogen gas 3) whenever possible purification procedures were performed in the dark or low light, and 4) the preparations were stored in the dark under argon. OxLDL was prepared by dialyzing 1 ml of LDL (4–10 mg/ml) (prepared without β-hydroxytoluene) against saline solution containing 5 µM $Cu_2SO_4$ (2×500 ml) for 24 to 48 hours at 4° C. Using a lipid peroxidation assay (El-Saadani et al., 1989), very little inadvertent oxidation in LDL and AcLDL preparations isolated with or without the precautions listed above was measured. Polyriboguanylic acid (poly G), polyriboinosinic acid (poly I), fucoidin, dextran sulfate, chondroitin sulfate, ReLPS (*S. minnesota* Re-595) and carrageenan (type III Kappa) were obtained from Sigma Chemical Co. Maleylated BSA (M-BSA) was prepared as described by Goldstein et al., 1979. The CD36 expression vector was a gift from B. Seed (Massachusetts General Hospital, Boston). 1,1'-dioctadecyl-3,3,3',3'-tetramethylindocarbocyanine perchlorate (DiI) and 3-pyrenemethyl-23,24-dinor-5-cholen-22-oate-3b-yl oleate (PMCAO) were obtained from Molecular Probes (Eugene, Oreg.) and were used to prepare fluorescently labeled AcLDL as described by Krieger et al., 1979 *J. Supra. Struct.* 10, 467–478; Krieger, 1986 *Meth. Enzymol.* 128, 608–613; Pitas et al., 1985 *J. Cell. Biol.* 100, 103–117; Kingsley and Krieger, 1984 *Proc Natl. Acad. Sci. USA* 88, 7844–7848. Compactin and dioctadecylamidoglycylspermine (DOGS) were generous gifts from A. Endo and J. R. Falck, respectively.

Cell Culture and Transfections.

CHO, ldlA (clone 7) and COS M6 cells were grown in culture as described by Krieger et al., 1983 *Proc. Natl. Acad. Sci. USA* 80, 5607–5611; Acton et al., 1993. All incubations with cells were performed at 37° C. in a humidified 5% $CO_2$/95% air incubator unless otherwise noted. COS M6 cells were grown in Dulbecco's Modified Eagle's Medium (DMEM) with 10% fetal bovine serum (FBS), 100 units/ml penicillin, 100 µg/ml streptomycin, and 2 mM glutamine (medium A). For transient transfections other than in the expression cloning experiments, $1 \times 10^6$ COS cells were plated in 100 mm dishes in medium A on day 0. On day 1, plasmid DNA (between 2 and 10 µg in 1.9 ml phosphate buffered saline [PBS, calcium/magnesium free]) was mixed with 100 µl of 10 mg/ml DEAE-dextran (Pharmacia) and then added to each dish, which was then incubated at 37° C. with gentle shaking every 10 minutes. After 30 minutes, 8 ml of medium A supplemented with 80 µM chloroquine (Sigma) were added and the cells were incubated for another 2.5 hrs. The medium was removed and the cells were shocked with 5 ml of 10% (v/v) dimethylsulfoxide in medium A for 2.5 minutes. This medium was quickly removed by aspiration, the cells were washed with 10 ml of PBS (containing calcium and magnesium), and 10 ml of fresh medium A were added. On day 2 the cells were harvested with trypsin and replated (0.5–$1 \times 10^6$ cells/well in 6-well dishes) in medium A containing 1 mM sodium butyrate. On day 3, the cells were assayed for ligand binding at 4° C. and for binding plus uptake (binding/uptake) and degradation at 37° C. Stable transfections were performed as follows: ldlA cells were plated at $1 \times 10^6$ cells per 100 mm dish in medium B (Ham's F12 containing 100 units/ml penicillin, 100 µg/ml streptomycin, and 2 mM glutamine) supplemented with 10% fetal calf serum. On day 2, the cells were washed three times with medium B. A complex of DNA and DOGS (dioctadecylamidoglycylspermine, which was a gift from J. R. Falck) was prepared by adding 150 µl of a DNA solution (12 µg of plasmid and 1.2 µg of supercoiled pSV2neo in 300 mM NaCl) to 150 µl of solution A (0.33 mg/ml DOGS, 300 mM NaCl). The DNA/DOGS complex was added to the cells in 3.6 ml of serum-free Opti-MEM medium (GIBCO) containing penicillin (100 U/ml) and streptomycin (100 µg/ml). After a 14 hr transfection period, the cells were washed three times with medium B and incubated in medium B plus 10% fetal calf serum for one day before being replated at a density of $3 \times 10^6$ cells per 100 mm dish. One day later, the culture medium was replaced with selection medium, medium B supplemented with 10% fetal calf serum and 0.25 mg/ml G418. This medium was changed every two to three days, and G418-resistant colonies appeared 10 to 12 days after transfection. The colonies were screened for DiI-AcLDL endocytosis and positive colonies were picked and grown to mass culture for further analysis.

Isolation of Var-261 Cells.

Var-261 cells, a rare spontaneously arising variant expressing a novel scavenger receptor activity, were isolated during a transfection/selection experiment as follows. Human liver genomic DNA prepared as described by Sege et al., 1984 *Nature* 307, 742–745, was transfected into ldlA (clone 7) cells, a CHO cell mutant clone whose defective LDL receptor gene results in an essentially LDL receptor-negative phenotype (Sege, et al., 1986 *Mol. Cell. Biol.* 6, 3268–3277; Kingsley et al., 1986 *Mol. Cell. Biol.* 6, 2734–2737; Kingsley and Krieger, 1984). After transfection, variants expressing scavenger receptor activity were isolated by growing the cells in MAC selection medium (Penman et al., 1991 *J. Biol. Chem.* 266, 23985–23993) [250 µM Mevalonate, 3 µg protein/ml of AcLDL, 40 µM Compactin, and 3% (v/v) newborn calf lipoprotein-deficient serum in medium B. In MAC medium, endogenous cholesterol synthesis is inhibited by compactin and only those cells that are able to obtain cholesterol by the endocytosis of AcLDL can survive. The parental ldlA cells used for the transfection cannot grow in MAC medium. After incubation in MAC medium for 29 days, surviving colonies were re-fed with medium B supplemented with 3% (v/v) newborn calf lipoprotein-deficient serum containing AcLDL which was fluorescently labeled by reconstitution of the lipid core (Krieger, 1986) with the pyrene-based lipophilic dye PMCAO (Krieger et al., 1979). Colonies which accumulated significant amounts of fluorescence from the lipoprotein, as determined by fluorescence microscopy (Krieger et al., 1981 *J. Mol. Biol.* 150, 167–184), were harvested and maintained in MAC selection medium. One colony, designated Var-261, exhibited significant levels of AcLDL binding, uptake and degradation activity which were dramatically greater than those in either the parental ldlA cells or any of the other colonies. Southern blot analysis using human genomic DNA as a probe showed that there was no detectable human-specific repeat DNA in Var-261 cells. Thus, Var-261 cells are presumably rare, spontaneously arising variants which express an endogenous hamster scavenger receptor gene. This expression could be due to the activation of an otherwise silent gene. Alternatively, it might be due to a spontaneous mutation which conferred novel activity on an endogenous protein with some other function (e.g., see Faust and Krieger, 1987 *J. Biol. Chem.* 262, 1996–2004, and Chen et al., 1990 *J. Biol. Chem.* 265, 3116–3123).

$^{125}$I-AcLDL Binding, Uptake and Degradation Assays.

Scavenger receptor activities at 37° C. were measured by ligand binding, uptake and degradation assays as described by Krieger, 1983; Freeman et al., 1991). Although binding and uptake at 37° C. were determined separately using dextran-sulfate to free surface bound lipoproteins from the cells as described for LDL receptor assays by Goldstein et al., 1983; Basu et al., 1983 *Science* 219, 871–873), this method for separating bound from internalized ligand for $^{125}$I-AcLDL and scavenger receptors has not been independently validated. Accordingly, the values for binding and uptake were combined and are presented as binding plus uptake observed after a 5 hour incubation and are expressed as ng of $^{125}$I-AcLDL protein per 5 hr per mg cell protein. Degradation activity is expressed as ng of $^{125}$I-AcLDL protein degraded in 5 hours per mg of cell protein. The specific, high affinity values presented represent the differences between the results obtained in the presence (single determinations) and absence (duplicate determinations) of excess unlabeled competing ligand (75 to 200 µg/ml of M-BSA). Cell surface 4° C. binding was assayed using either method A or method B as indicated. In method A, cells were prechilled on ice for 15 min, re-fed with $^{125}$I-AcLDL in ice-cold medium B supplemented with 10% (v/v) fetal bovine serum, with or without 75–200 µg/ml unlabeled M-BSA, and incubated 2 hr at 4° C. on a shaker. Cells were then washed rapidly three times with Tris wash buffer (50 mM Tris-HCl, 0.15 M NaCl, pH 7.4) containing 2 mg/ml BSA, followed by two 5 min washes, and two rapid washes with Tris wash buffer without BSA. The cells were solubilized in 1 ml of 0.1 N NaOH for 20 min at room temperature on a shaker, 30 µl were removed for protein determination, and the radioactivity in the remainder was determined using a LKB gamma counter. Method B differed from method A in that the cells were prechilled for 45 minutes, the medium contained 10 mM HEPES and 5% (v/v) human lipoprotein-deficient serum rather than fetal bovine serum, and the cell-associated radioactivity released by treatment with dextran sulfate was measured as described by Krieger, 1983; Freeman et al., 1991).

Preparation of Var-261 cDNA Library.

Poly A$^+$ mRNA was isolated from Var-261 cells using standard procedures (Sambrook, Fritsch, and Maniatis. *Molecular Cloning: A Laboratory Manual*. Cold Spring Harbor, N.Y., Cold Spring Harbor Laboratory Press (1989)). This mRNA was used to synthesize double-stranded cDNA using a Not I unidirectional primer (Invitrogen) according to the method of Aruffo and Seed, 1987 *Immunology* 84, 8573–8577. BstXI linkers (Invitrogen) were added to the cDNA. The isolated cDNA was digested with Not I, size selected from agarose gels (in three size groups: 1 to 2 kb, 2 to 4 kb, greater than 4 kb), and ligated into the expression vector pcDNA I (Invitrogen). The average insert size for the entire Var-261 unidirectional library was approximately 1.5 kb. The DNAs for transfection experiments were prepared as follows. *E. coli* strain MC1061/P3 was transformed with the cDNA expression plasmids by electroporation and the transformed cells were plated on LB-A/T plates (Luria broth with ampicillin (15 µg/ml)/tetracycline (8 µg/ml)) (Sigma) to obtain isolated colonies at densities of approximately 5,000 per 150 mm dish. Each plate, representing one pool, was scraped to recover the bacteria and a pool of library plasmids was isolated from each bacterial mixture using a midiprep method (miniprep method scaled up 5 to 10 fold (Sambrook et al., 1989)).

Expression Cloning by Transient Expression in COS Cells.

On day 0, COS M6 cells were plated in 35 mm culture dishes (3 to 4×10$^5$ cells/dish) in medium A. On day 1, the cells in each dish were transfected with 0.5 µg/dish of expression library DNA from a single pool following the DEAE-dextran method of Cullen 1987 *Methods in Enz.* 152, 684–704. On day 2, monolayers were re-fed with medium A containing 1 mM sodium butyrate (modified medium A). On day 3, the monolayers were re-fed with modified medium A containing one to five µg protein/ml of DiI-labeled AcLDL (DiI-AcLDL). After a 5 hr incubation at 37° C., the plates were washed two times with PBS and the cells were fixed with 3.7% formaldehyde in PBS for 10 min at room temperature. The presence of fluorescent DiI in the fixed cells was determined by visual inspection using a Leitz inverted fluorescence microscope with a rhodamine filter package as described by Kingsley and Krieger, (1984). Each transfection experiment included negative control transfections with empty vector pcDNA I (0 to 20 DiI-positive cells per dish) and positive control transfections with a mixture of a pcDNA I-based bovine type II macrophage scavenger receptor expression vector, pXSR3 (Rohrer et al., 1990) and the empty vector pcDNA I (1:5000 ratio, 200 to 400 DiI-positive cells per dish). A positive pool was serially subdivided and retested to permit the purification of the single positive plasmid, phaSR-BI.

Northern Blot Analysis.

0.5 micrograms of poly(A)+ RNA prepared from different murine tissues or from 3T3-L1 cells on zero, two, four, six or eight days after initiation of differentiation into adipocytes as described by Baldini et al., 1992 *Proc. Natl. Acad. Sci. U.S.A.* 89, 5049–5052, was fractionated on a formaldehyde/agarose gel (1.0%) and then blotted and fixed onto a Biotrans™ nylon membrane. The blots were hybridized with the indicated probes that were $^{32}$P-labeled (2×10$^6$ dpm/ml, random-primed labeling system). The hybridization and washing conditions, at 42° C. and 50° C., respectively, were performed as described by Charron et al., 1989 *Proc. Natl. Acad. Sci. U.S.A.* 86, 2535–2539. The probe for haSR-BI mRNA analysis was a 0.6 kb BamHI fragment from the cDNA's coding region. The coding region of murine cytosolic hsp70 gene (Hunt and Calderwood, 1990 *Gene* 87, 199–204) was used as a control probe for equal mRNA loading.

SR-BI protein in tissues was detected by blotting with polyclonal antibodies to SR-BI.

HDL Binding Studies

HDL and VLDL binding to SR-BI and CD36 were conducted as described for LDL and modified LDL.

Studies conducted to determine if the HDL which is bound to SR-BI is degraded or recycled and if lipid which is bound to the HDL is transferred into the cells were conducted using fluorescent lipid-labeled HDL and $^{125}$I-HDL added to cultures of transfected or untransfected ldlA-7 at a single concentration (10 µg protein/ml). HDL associated with the cells was measured over time. A steady state was reached in approximately thirty minutes to one hour. A fluorescent ligand, DiI, described above with reference to LDL, was used as a marker for lipid (for example, cholesterol or cholesterol ester) uptake by the cell. Increasing concentration of DiI indicates that lipid is being transferred from the HDL to the receptor, then being internalized by the cell. The DiI-depleted HDL is then released and replaced by another HDL molecule bound to lipid.

Phospholipid Binding and Competition Assays

Materials—Reagents (and sources) were acetic subhydride (Mallinckrodt, Inc., Paris, Ky.); egg phosphatidylcholine, egg phosphatidic acid, liver phosphatidylinositol, brain phosphatidylserine, egg phosphatidylethanolamine, and brain sphingomyelin (Avanti Polar Lipds, Inc., Alabaster, Ala.); polycarbonate membrane filters (Poretica Corp., Livermore, Calif.); sodium [$^{125}$I]iodide and 1,2-dipalmitoyl-L-3-phosphatidyl [N-methyl-$^3$H] choline ([$^3$H]DPPC) (Amersham Corp.); DEAE-dextran (Pharmacia Biotech. Inc., Ham's F-12 medium, Dulbecco's modified Eagle's medium, fetal bovine serum, and trypsin/EDTA ((JRII Bio-science, Lenera, Kans.); and penicillin/streptomycin, glutamine, and GIBCO BRL G-418 sulfate (Life Technologies, Inc.). All other reagents and supplies were purchased from Sigma or were obtained as described previously (Krieger, 1983). Human LDL, AcLDL, $^{125}$I-labeled LDL, and $^{125}$I-labeled AcLDL (90–300 cpm/ng protein) were prepared essentially as described previously (Goldstein et al., 1983; Krieger, 1983; Acton et al., 1994).

Phospholipid Liposome Preparation. Unilamellar liposomes were made by extrusion through policarbonate membranes, (Szoka et al., 1980). Phospholipid liposomes were prepared containing the indicated phospholipid, phosphatidycholine, and free cholesterol in a molar ratio of 1:1:1. The lipids were mixed in chloroform and dried by rotary evaporation for 30 min. For preparation of radiolabeled liposomes, 50–75 μCi of [$^3$H]DPPC(62 Ci/mmol) were added to the lipid mixtures before drying. The dried lipids were resuspended in 150 mM NaCl, 0.1 mM EDTA, 10 mM HEPES, pH 7.5 (Buffer A). Once the samples were fully hydrated, they were extruded through 0.1-μ pore size polycarbonate membranes using a mini-extruder device (Avanti Polar Lipids, Inc., Alabaster, Ala.). After extrusion, liposomes were dialyzed against Buffer A and then stored under nitrogen at 4° C. until use. Liposomes were used within 2 weeks of preparation. The final phospholipid concentration was determined by the method of Bartlett (1959). The average diameters of unlabeled liposomes, which were determined from either two or three independent preparations using light scattering with a Coulter N4 plus light scatterer apparatus (Coulter Electronics Inc., Hialeah, Fla.), were: PS, 105; PC, 114: PA, 125; PE, 129; P1, 113; and SM, 131 nm. The number of phospholipid molecules/PS liposome was calculated as follows. Cross-sectional areas for cholesterol and phospholipid molecules in hydrated bilayers are assumed to be 0.35 nm$^2$ and 0.47 nm$^3$, respectively (Levine and Wilklus, 1971); assuming an homogenous distribution of the components throughout the PS/PC/cholesterol (1:1:1) liposomes, 73% of the surface area $(4\Pi r^2 \times 2$ (bilayer)$\times 0.73 = 50477$ nm$^2$) was phospholipid, or 107,398 phospholipid molecules/liposome (50477 nm$^2$/0.47 nm$^2$). Based on an average phospholipid mass of 785 g/mol, a liposome concentration of 10 μg phospholipid/ml converts to 0.12 nM in liposome particles.

Ligand Binding Assays. On Day 0, ldlA and ldlA[haSR-BI] cells were plated (2.5×10$^6$ cells/well in six-well dishes) in medium A or B, respectively, and the assay was performed on day 2. Transfected COS cells were prepared as described above. Binding assays were performed as described above, with the following minor modifications. Cells were pre-chilled on ice for 30 min., incubated with the indicated radiolabeled ligands ($^{125}$I-LDL, $^{125}$I-AcLDL, or $^3$H-labeled liposomes) in ice-cold medium D (Ham's F-12 containing 0.5% (w/v) fatty acid free bovine serum albumin (FAF-BSA) and 10 mM HEPES, pH 7.4), with or without unlabeled competitors, for 2 h at 4° C. with gentle shaking. Cells were then washed twice with Tris wash buffer (60 mM Tris-HCl, 0.15 M NaCl, pH 7.4) containing 2 mg/ml FAF-BSA, followed by one rapid wash with Tris wash buffer without FAF-BSA. The cells were then solubilized with 0.1 N NaCl, and radioactivity and protein determinations were made as described above. The specific, high affinity ligand binding activities shown represent the differences between values obtained in the absence (total binding) and presence (nonspecific binding) of an excess of the indicated unlabeled ligands. Nonspecific binding of [$^3$H]PS liposomes to cells were generally low. The binding values are expressed as nanograms of bound $^{125}$I-labeled protein or ng of total phospholipids from $^3$H-labeled liposomes/milligram of cell protein.

Other Procedures.

Protein concentrations were determined by the method of Lowry et al. 1951 *J. Biol. Chem.* 193, 265–275. DNA sequencing was performed using Sequenase 2.0 kit according to manufacturers instructions and the reported results for the coding region were verified by determining the sequence from both strands of the template. Oligonucleotide primers were prepared in the MIT Biopolymers Laboratory. Polymerase chain reaction (PCR) was used to generate a fragment of the hamster class A scavenger receptor DNA as follows. Primers based on the sequence of one exon of the murine scavenger receptor gene (Ashkenas et al., 1993 *J. Lipid Res.* 34, 983–1000) (5' AATGAAGAACTGCT-TAGTTT 3' (Sequence ID No. 1) and 5' AATCAAGGAATT-TAACTG 3' (Sequence ID No. 2)) were used to amplify a fragment of the expected size (240 base pairs) from hamster ldlA cell genomic DNA. This amplicon was cloned into pCR1000 (Invitrogen) to generate the plasmid pSA1, which was sequenced.

Results

Isolation and Characterization of Variant Var-261

High Affinity Binding, Uptake and Degradation of AcLDL

The LDL receptor-deficient CHO cell line ldlA was processed and subjected to nutritional selection for rare variants which expressed endocytic receptors for AcLDL. One of the isolates, designated Var-261, was examined further. Var-261 and ldlA cells were plated on day 0 at 350,000 and 250,000 cells/well, respectively, in 6-well dishes in medium B plus 3% (v/v) newborn calf lipoprotein-deficient serum, and assayed on day 2 as described above. $^{125}$I-AcLDL binding at 4° C. for 2 hrs was measured using method B. $^{125}$I-AcLDL binding plus uptake and degradation at 37° C. was measured after a 5 hr incubation. The high affinity values shown represent the differences between measurements made in the absence (duplicate incubations) and presence (single incubations) of an excess of the unlabeled competitor M-BSA (100 μg/ml).

Figure 2A:
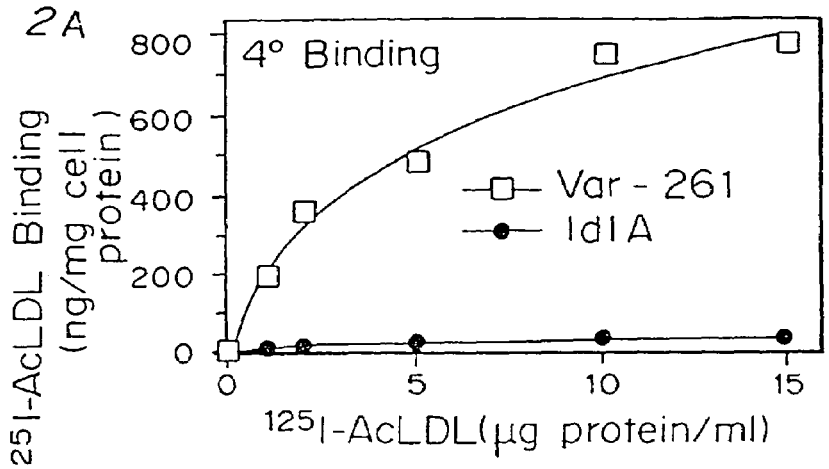
FIGS. 2A, 2B, and 2C are graphs of the concentration dependence of $^{125}$I-AcLDL interaction with control cells, Var-261 and ldlA-7 (LDL receptor deficient control cells, also referred to as ldlA cells) cells, at 4° C. and 37° C.
Figure 2B:
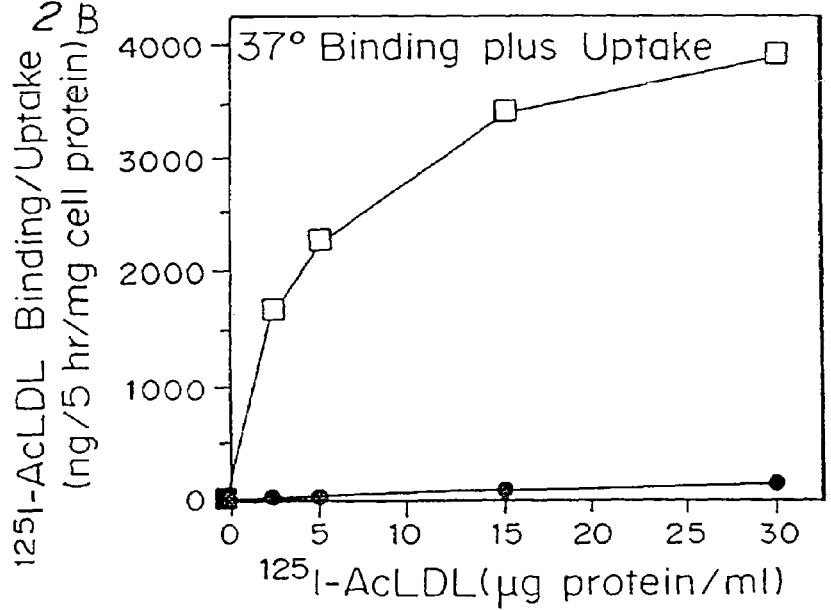
Figure 2C:
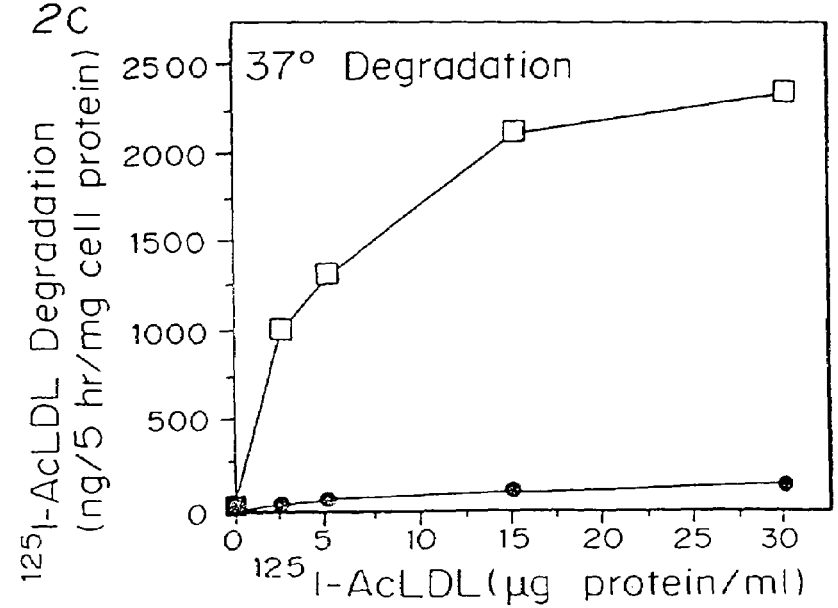

As shown by FIG. 2A, these cells exhibited high affinity, saturable $^{125}$I-AcLDL binding at 4° C. The binding at 37° C. and subsequent uptake shown in FIG. 2B and lysosomal degradation shown in FIG. 2C were characteristic of receptor-mediated endocytosis. Degradation, but not binding plus uptake, at 37° C. was inhibited by the lysosomotrophic drug chloroquine. In contrast, there was virtually no high affinity binding, uptake, or degradation of $^{125}$I-AcLDL by the parental ldlA cells or wild-type CHO cells. The scavenger receptor activity in Var-261 cells was not suppressed by the addition of sterols to the medium.

Broad Polyanion Binding Specificity

A hallmark of macrophage scavenger receptors is their broad polyanion binding specificity, usually assessed by competition with polyanionic ligands for $^{125}$I-AcLDL binding, uptake and degradation. For further characterization, the ligand specificity of the scavenger receptor activity of Var-261 cells was compared with that of transfected COS cells transiently expressing the murine type II macrophage scavenger receptor, a class A scavenger receptor (mSR-AII).

COS cells were transfected on day 1 with murine scavenger receptor type II. On day 2 the transfected COS cells and Var-261 cells were set in 6-well dishes ($1 \times 10^6$ and $0.5 \times 10^6$ cells/well, respectively). On day 3, $^{125}$I-AcLDL (5 µg/ml) in medium B plus 10% fetal bovine serum was added to the cells and degradation was measured after a 5 hr incubation at 37° C. in the absence (duplicate determinations) or presence (duplicate determinations) of the indicated amounts of polyanions. The 100% of control values (ng/5 hr/mg cell protein) from the two experiments were: Var-261, 606 and 473; and COS[mSR-AII], 1982 and 976. For the Var-261 and COS[mSR-AII] cells, the 100% of control values were: 321 and 390; and 848 and 1014, respectively.

The classic scavenger receptor polyanionic ligands AcLDL, fucoidin, and poly G were all effective competitors of $^{125}$I-AcLDL degradation by both Var-261 and the transfected COS cells, and native LDL did not inhibit the activity in either cell type. Nevertheless, the binding specificity in Var-261 cells differed from that in macrophages and for class A receptors in several critical ways. Poly I, a very effective competitor of class A scavenger receptors (greater than 50% inhibition at 2.5 µg/ml) only partially inhibited the activity in Var-261 cells (34% inhibition at 400 µg/ml). In contrast, maleylated BSA (M-BSA) inhibited the scavenger receptor activity in Var-261 cells at concentrations far lower that those required for inhibition of the murine type II receptors. The ReLPS form of endotoxin, which is a scavenger receptor competitor exhibiting complex binding properties for class A scavenger receptors (Ashkenas et al., 1993), only partly inhibited the activity in Var-261 cells at the high concentration of 250 µg/ml.

Determination if Hamster Scavenger Receptor DNA is Expressed in Var-261 Cells

The striking differences in ligand specificities between the scavenger receptor activity in Var-261 cells and those exhibited by the murine and bovine class A scavenger receptors (Ashkenas et al., 1993; Kodama et al., 1990; Rohrer et al., 1990) strongly suggested that the Var-261 cells did not express class A receptors. However, there was a possibility that the novel specificity was merely a consequence of species differences (e.g., hamster-derived Var-261 cells vs. murine SR-AII). To determine if this was the case, a 240 base pair fragment of the hamster class A macrophage scavenger receptor gene was isolated by polymerase chain reaction (PCR) using genomic CHO cell DNA as a template. This hamster gene fragment, which is found in both type I and II macrophage scavenger receptors, was cloned and sequenced. This fragment has between 75%–85% nucleotide sequence identity with its human, murine, rabbit and bovine counterparts (Kodama et al., 1990; Rohrer et al., 1990; Ashkenas et al., 1993; Matsumoto et al., 1990 *Proc. Natl. Acad. Sci. USA* 87, 9133–9137; Bickel and Freeman, 1992) and, with the exception of the amino acid corresponding to murine position 117, was consistent with the previously identified consensus sequence defined for residues 95–159 (Ashkenas et al, 1993).

This hamster fragment was used as a probe in Northern analysis of Var-261 cell mRNA. Under conditions where the hamster probe recognized murine scavenger receptor mRNA from CHO cells transfected with the murine scavenger receptor cDNA (Ashkenas et al., 1993), no signal was detected in the hamster-derived Var-261 or control CHO cell mRNA, even after extensive overexposure of the film. Thus, Var-261 cells do not express significant amounts of the hamster type I or II class A receptors and must instead express a different scavenger receptor.

Cloning of haSR-BI Receptor cDNA from Var-261

In an attempt to clone a cDNA encoding this apparently new scavenger receptor, a cDNA expression library was prepared from Var-261 poly A$^+$ mRNA, the library was divided into small pools (approximately 5000 clones/pool), the pools were transfected into COS cells and the transiently transfected cells visually screened for endocytosis of fluorescent AcLDL (DiI-AcLDL). A receptor-positive pool was obtained after screening approximately 450,000 clones and this pool was subdivided repeatedly until a single functional plasmid (designated phaSR-BI for plasmid encoding hamster scavenger receptor type BI) was obtained.

Figure 3A:
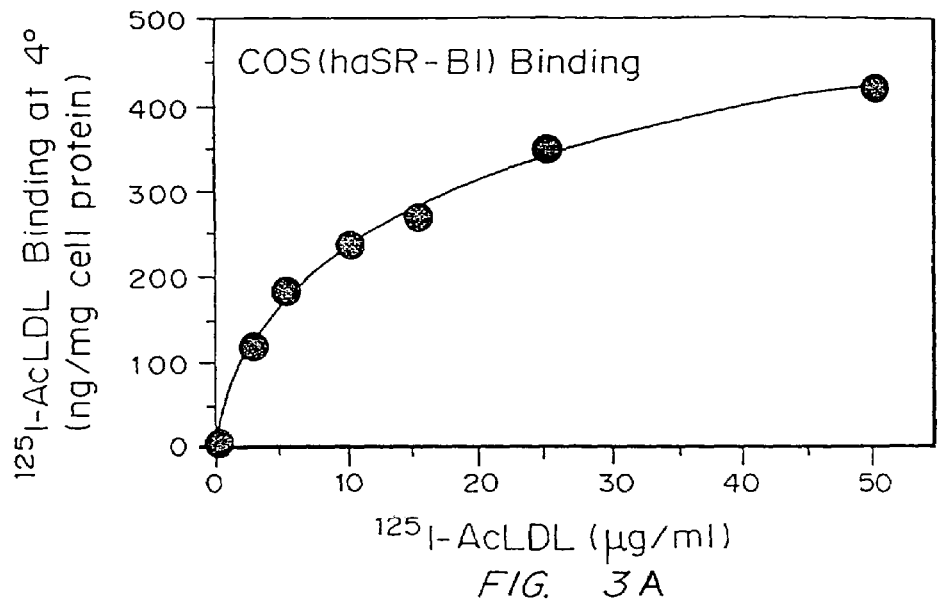
FIGS. 3A and 3B are graphs of the binding of $^{125}$I-AcLDL to haSR-BI expressed in transfected COS cells which do not otherwise express SR-BI (FIG. 3A) and specificity of binding of $^{125}$I-AcLDL to Var-261 and ldlA [haSR-BI] cells (FIG. 3B) measured as the percent of control binding in the presence of competitor: M-BSA (10 µg/ml), poly G (500 µg/ml), Fucoidin (200 µg/ml), Carrageenan (200 µg/ml), and LDL (500 µg/ml).
Figure 3B:
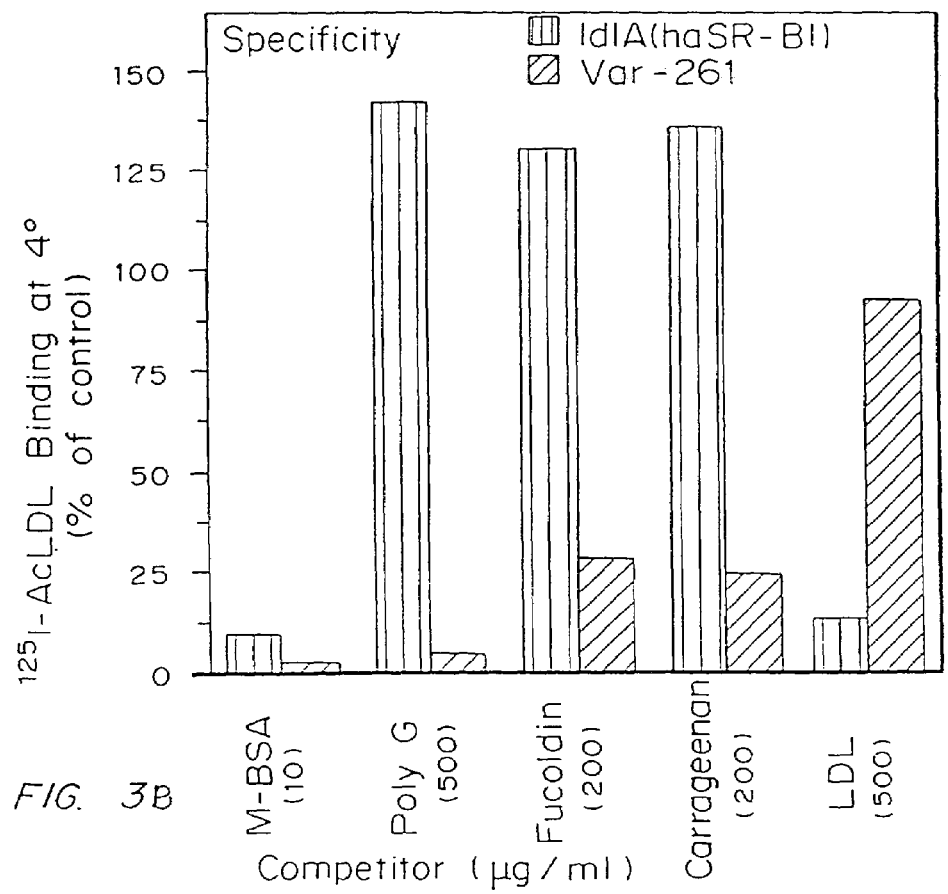

FIGS. 3A and 3B are graphs of $^{125}$I-AcLDL binding to haSR-BI expressed in transfected COS cells: FIG. 3A demonstrates the concentration dependence in COS[haSR-BI] cells and FIG. 3B demonstrates the ligand specificity in ldlA[haSR-BI] cells. To measure binding of AcLDL, on day 1, COS cells were transfected with the expression vector for the hamster scavenger receptor type BI (haSR-BI). On day 2 the transfected COS cells were plated in 6-well dishes ($1 \times 10^6$ cells/well in medium A plus 1 mM sodium butyrate). On day 3 between 0 and 50 µg/ml of $^{125}$I-AcLDL were added to the monolayers at 4° C. and binding was measured using Method A. The high affinity values shown in the Figures represent the differences between measurements made in the absence (duplicate incubations) and presence (single incubations) of an excess of the unlabeled competitor M-BSA (200 µg/ml). To measure binding specificity, on day 1, Var-261 and ldlA[haSR-BI] cells were plated in 6-well dishes ($0.2 \times 10^6$ cells/well in MAC medium or medium B containing 10% fetal bovine serum and 0.25 mg/ml G418, respectively). On day 3 the binding of $^{125}$I-AcLDL (5 µg/ml) at 4° C. in the absence or presence of the indicated competitors was measured using Method A. The values shown in the Figures represent the averages of duplicate determinations. The 100% of control values for Var-261 and ldlA [haSR-BI] were 1809 and 293 ng/mg cell protein, respectively.

The HaSR-BI plasmid conferred high affinity ($K_d$(4° C.) approximately 5 µg protein/ml) $^{125}$I]-AcLDL binding on transiently transfected COS cells, as shown by FIG. 3A. The ligand specificity of haSR-BI expressed in stably transfected ldlA cells was compared to that of the Var-261 cells, as shown in FIG. 3B. M-BSA inhibited the binding of $^{125}$I-AcLDL to cells expressing haSR-BI and to Var-261 cells. Unexpectedly, haSR-BI was not inhibited by poly G, fucoidin or carrageenan (another classic scavenger receptor ligand (Brown and Goldstein, 1983)), which were competitors for the activity in Var-261 cells. In addition, LDL did not inhibit the binding of $^{125}$I-AcLDL to Var-261 cells, but was a competitor for cells expressing haSR-BI. There is no other case in which native LDL has been reported to block scavenger receptor activity. Thus, the specificity of the haSR-BI differs dramatically from that reported for any previously described scavenger receptor, including that in Var-261 cells. Since the ligand specificities of the class B receptors described in more detail below are very different from the activity in Var-261 cells, it seems unlikely that either of these two class B scavenger receptors accounts for the binding activity observed in the Var-261 cells.

Northern blot analysis using haSR-BI as a probe showed that a single major mRNA (approximately 3.4 kb) was present in similar amounts in both the parental ldlA and Var-261 cells, indicating that the cells express similar amounts of haSR-BI mRNA. Therefore, although haSR-BI encodes a scavenger receptor, it is apparently expressed in both ldlA and Var-261 cells at very low levels. Taken together with the specificity data described above, these results indicate that haSR-BI is a novel scavenger receptor which was not responsible for most of the scavenger receptor activity in Var-261 cells.

Analysis of haSR-BI cDNA

The cloned haSR-BI cDNA is approximately 2.9 kb long. The sequences of the 5' untranslated region, the coding region, and a portion of the 3' untranslated region are shown in Sequence Listing ID No. 3. The predicted protein sequence is 509 amino acids (Sequence Listing ID No. 4) with a calculated molecular weight of 57 kD. The murine cDNA was subsequently isolated. The nucleotide sequence is shown in Sequence Listing ID No. 7 and the predicted amino acid sequence is shown in Sequence Listing ID No. 8.

Based on comparison of amino acid sequence, haSR-BI has homology along its entire length to members of the CD36 family of membrane proteins: CD36 (32%, 31% and 33% amino acid identities with the human (Oquendo et al., 1989), murine (Endemann et al., 1993) and rat (also known as "FAT", Abumrad et al., 1993) homologs), rat LIMPII (33%, a lysosomal integral membrane protein (Vega et al., 1991 *J. Biol. Chem.* 266, 16818–16824), and two *Drosophila melanogaster* proteins, emp (29%, Hart and Wilcox, 1993 *J. Mol. Biol.* 234, 249–253) and "dCD36" (31%, Genbank #DMCD361). All of these, with the exception of "dCD36", have two internal hydrophobic domains, which have been suggested to serve as membrane spanning domains, and a series of conserved cysteines and putative N-linked glycosylation sites (see Vega et al., 1991 for a description of the common sequence elements).

Characterization and Comparison of haSR-BI Binding with Human CD36 Binding Affinity and Selectivity To further characterize the binding properties of huCD36 and compare them with those of haSR-BI, the properties of COS cells transiently transfected with a cDNA expression vector for human CD36 (obtained from Dr. Brian Seed, Oquendo et al., 1989) were examined.

COS cells were transfected on day 1 with a plasmid encoding CD36. On day 2 the transfected cells were set in 6-well dishes at 1×10⁶ cells/well in medium A plus 1 mM sodium butyrate. On day 3, $^{125}$I-AcLDL binding at 4° C. was measured. The high affinity values shown represent the differences between measurements made in the absence (duplicate incubations) and presence (single incubations) of an excess of the unlabeled competitor M-BSA (200 μg/ml). On day 3, degradation of $^{125}$I-AcLDL (5 μg/ml) was measured after a 5 hr incubation at 37° C. in the absence (duplicate determinations) or presence (duplicate determinations) of the indicated competitors. The values represent the means of four determinations from two identical experiments (the error bars represent standard deviations). The 100% of control values (ng/5 hr/mg cell protein) from the two experiments were 232 and 103.

Figure 4A:
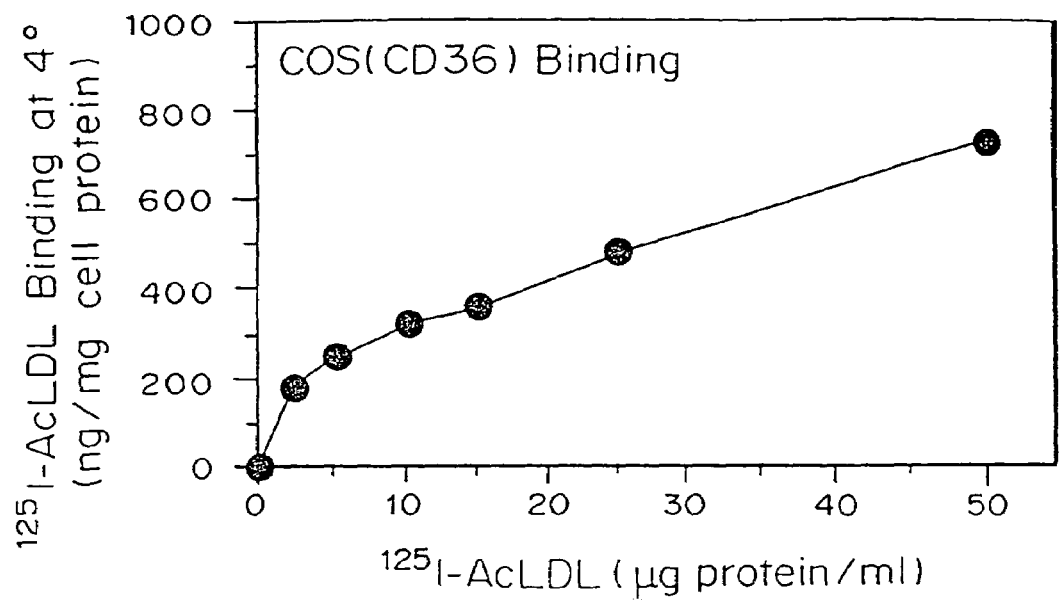
FIGS. 4A and 4B are graphs of the binding of $^{125}$I-AcLDL to CD36 expressed in transfected COS cells (FIG. 4A) and specificity of binding of $^{125}$I-AcLDL to transfected COS cells (FIG. 4B) measured as percent of control in the presence of a competitor: M-BSA (4 µg/ml), AcLDL (500 µg/ml), Fucoidin (200 µg/ml), Poly I (500 µg/ml), Poly G (500 µg/ml), and ReLPS (250 µg/ml).
Figure 4B:
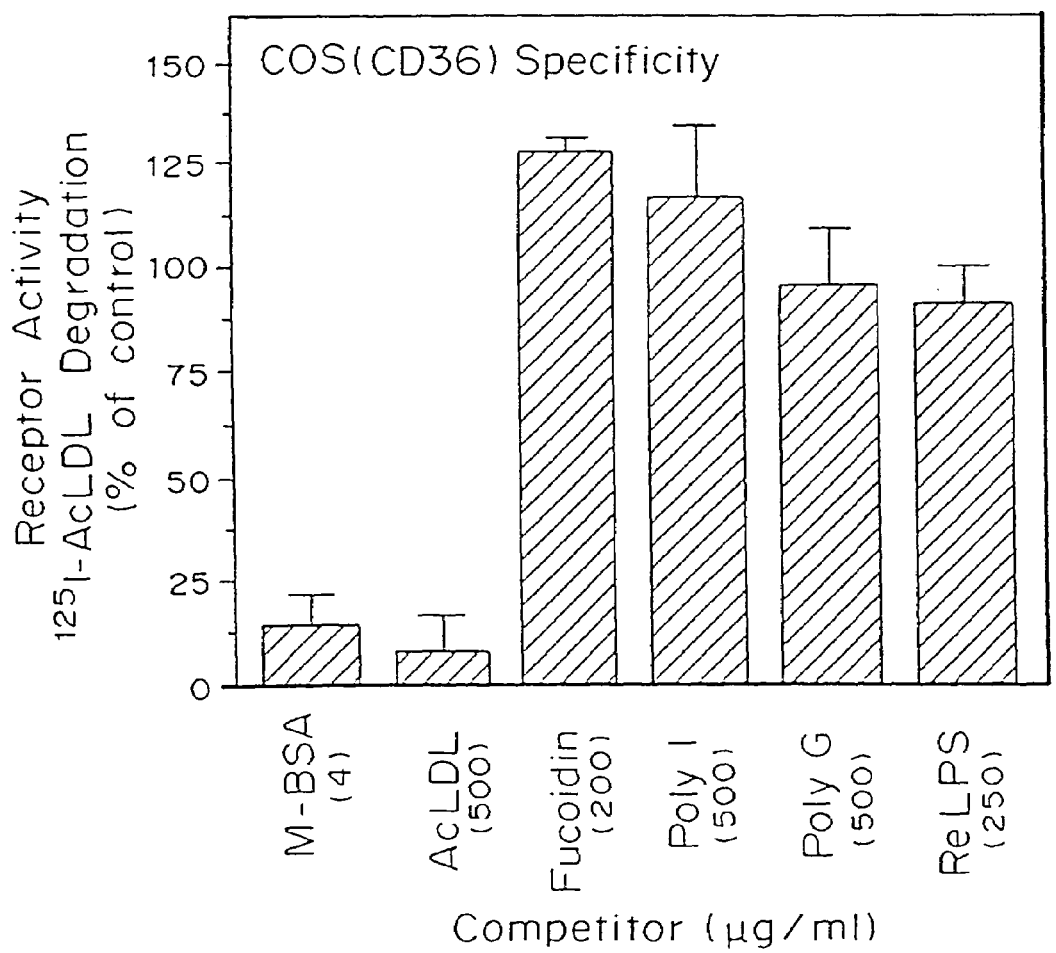
Figure 5:
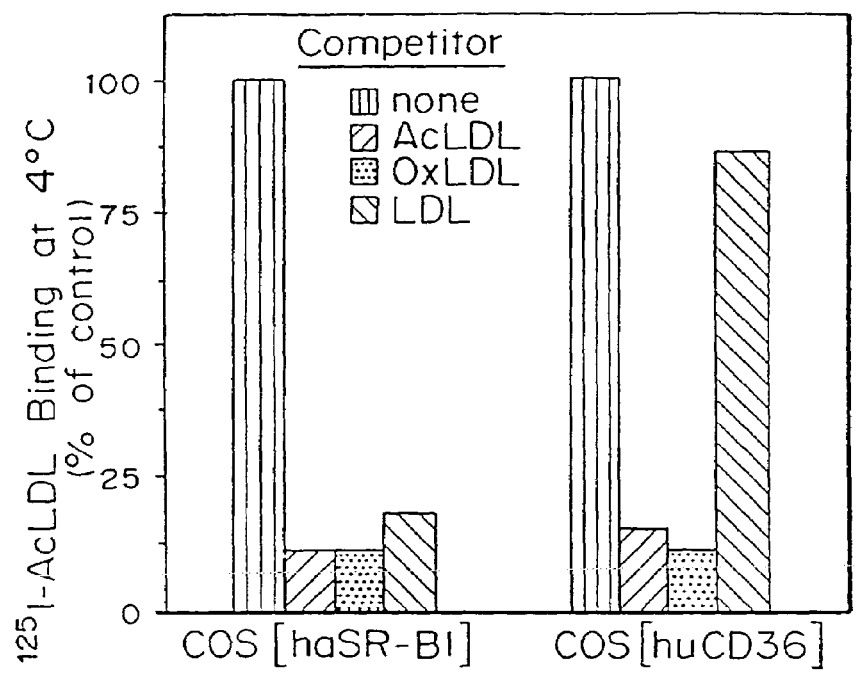
FIG. 5 is a graph of lipoprotein inhibition of $^{125}$I-AcLDL binding to haSR-BI and huCD36, measured as percent of control binding at 4° C., to either COS[haSR-BI] or COS [huCD36], alone, in the presence of AcLDL, OxLDL or LDL.

FIG. 4A shows that expression of huCD36 conferred high affinity $^{125}$I-AcLDL binding on transiently transfected COS cells at 4° C. with an apparent dissociation constant in the range of approximately 5 μg protein/ml. FIG. 4B shows that the receptor activity was inhibited by M-BSA and AcLDL, but not by other polyanions which inhibit class A macrophage scavenger receptors, including fucoidin, poly I, poly G, and ReLPS. FIG. 5 is a graph directly comparing lipoprotein inhibition of $^{125}$I-AcLDL binding to haSR-BI and huCD36. The graph clearly demonstrates the similarities: i.e., binding to both receptors is inhibited by the modified LDL; and the differences: only haSR-BI binding is inhibited by LDL.

HDL Binding to haSR-BI

Figure 8A:
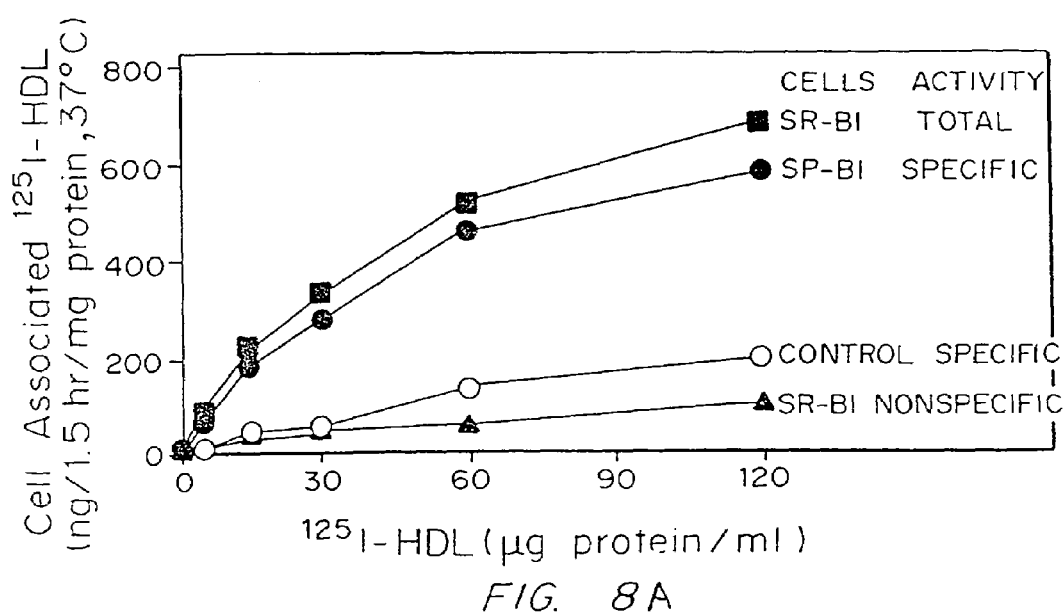
FIG. 8A is a graph of the cell associated $^{125}$I-HDL (ng/1.5 hr/mg protein, 37° C.) as a function of $^{125}$I-HDL (µg protein/ml), for SR-BI transfected CHO cells and untransfected controls (ldlA-7).

Further binding studies were conducted to determine if SR-BI bound HDL and VLDL, as well as LDL and anionic phospholipids. Competition binding studies demonstrate that HDL and VLDL (400 μg/ml) competitively inhibit binding of $^{125}$I-AcLDL to HaSR-BI, providing further support for the potential role of this receptor in lipoprotein and lipid metabolism. Direct binding of $^{125}$I-HDL to cells expressing SR-BI is shown in FIG. 8A. Studies were also conducted using CD36, which demonstrated that HDL bound competitively to CD36.

Phospholipid Binding

Figure 7A:
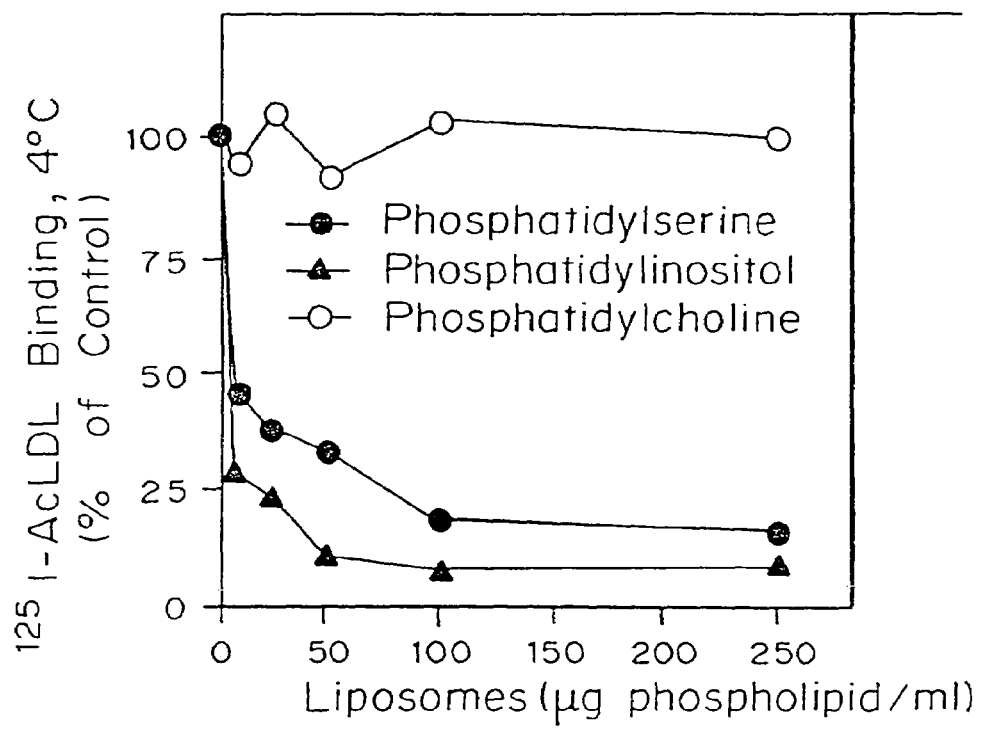
FIGS. 7A and 7B are graphs $^{125}$I-AcLDL binding, 4° C. (% of control) as a function of liposome concentration (µg phospholipid/ml) (PS, circles; PI, triangles; PC, open circles), haSR-BI, FIG. 7a; huCD36, FIG. 7b.
Figure 7B:
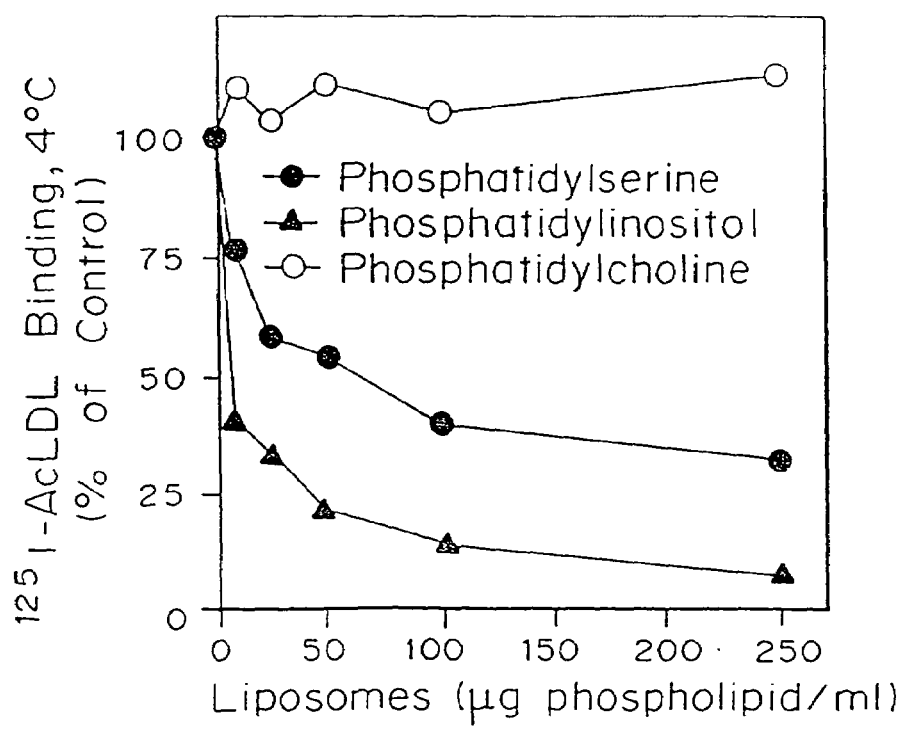
Figure 7C:
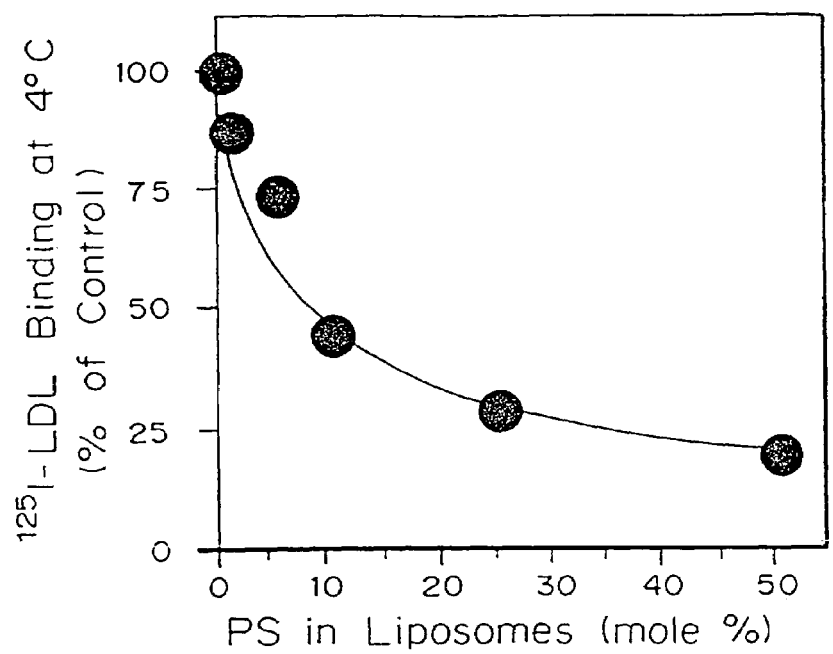
FIG. 7C is a graph of the effect of PS:PC ratio on inhibition of $^{125}$I-LDL binding to SR-BI, $^{125}$I-LDL binding at 4° C. (% of control) to PS in liposomes (mole %).
Figure 7D:
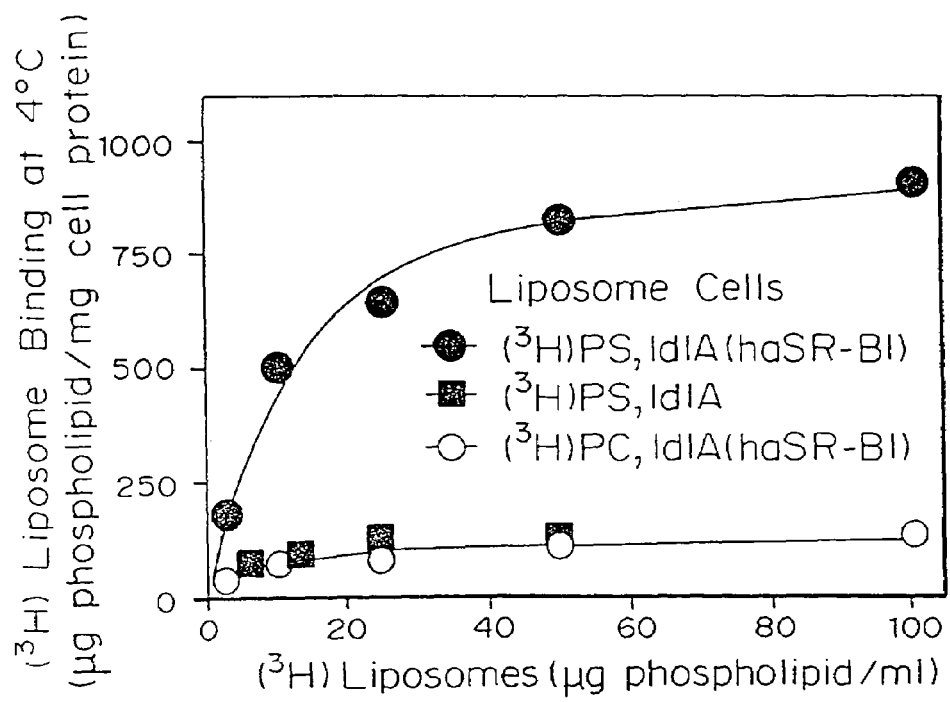
FIG. 7D is [$^3$H]-liposome binding to haSR-BI, [$^3$H]-liposome binding at 4° C. (µg phospholipid/mg cell protein) versus [$^3$H]-liposomes (µg phospholipid/ml) ([$^3$H]PS, ldlA [haSR-BI] (circles); [$^3$H]PS, ldlA (square); [$^3$H]PC, ldlA [haSR-BI] (open circles)).

To determine if phospholipids could bind to haSR-BI, 105 nm diameter PS liposomes (PS/phosphatidylcholine/cholesterol, ratio 1:1:1) radiolabeled with trace amounts of [$^3$H] dipalmitoyl phosphatidylcholine (62 Ci/mmol) were prepared and binding at 4° C. to untransfected cells (ldlA) and transfected cells which express haSR-B1 (ldlA[haSR-BI] cells determined. The results are shown in FIGS. 7A, 7B, 7C, 7D, and 7E. FIG. 7D shows that there was substantial, high affinity ($K_d$-15 μg phospholipid/ml) and saturable binding to the transfected cells, but relatively little binding to the untransfected cells. Assuming that the phospholipid and cholesterol were uniformly distributed in homogenous liposomes containing approximately 107,400 molecules of phospholipid/liposome, it is estimated that the $K_d$ (mol of PS liposomes/liter) to be approximately 0.18 nM. PS binding was apparently independent of divalent cations because it was not inhibited by EDTA (1–10 mM). Binding depended on the phospholipid composition of the liposomes. In contrast to that of [$^3$H]PS liposomes, the binding of radiolabeled PC liposomes (PC/cholesterol, 2:1) was very low and similar to [$^3$H]PS binding to untransfected ldlA cells.

Figure 7E:
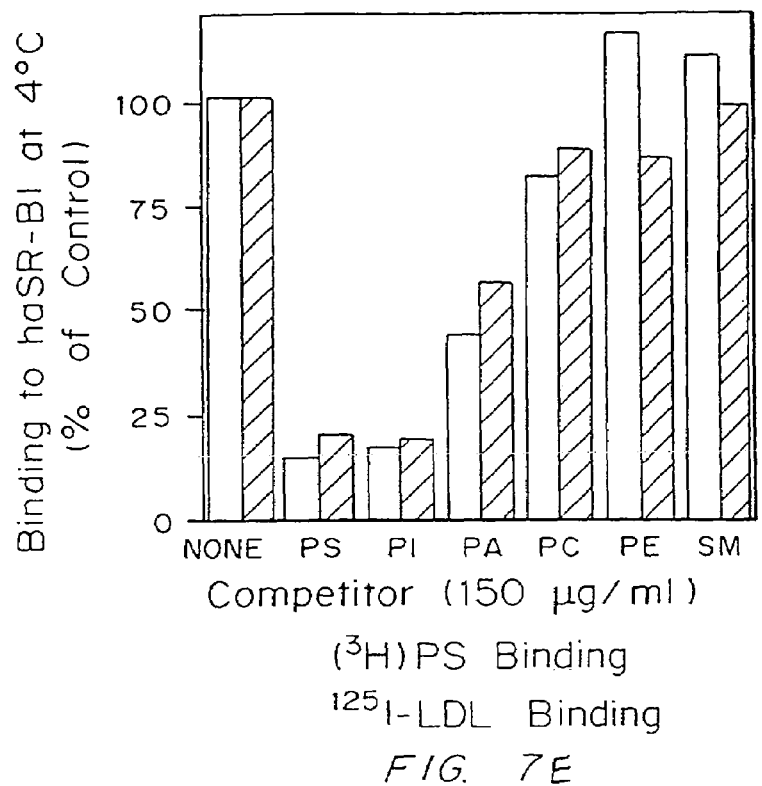
FIG. 7E is a graph of the specificity of binding to SR-BI, binding of haSR-BI at 4° C. (% of control) versus competitor (150 µg/ml), [$^3$H]PS (light bar) and $^{125}$I-LDL (dark bar).

These results indicated that phospholipids can bind to haSR-BI and that this binding might depend on the charge of the phospholipid head group. The specificity of the binding was further assessed by determining the competition for [$^3$H]PS binding by unlabeled liposomes of various compositions (indicated phospholipid/PC/cholesterol, ratio 1:1:1). FIG. 7E shows that the anionic phospholipids PS and PI were effective inhibitors while the zwitterionic PC and PE as well as SM were not. PA, another anionic phospholipid, was able to compete, but not as effectively as PS and PI. FIG. 7A shows that PS and PI liposomes inhibited virtually all of the binding of $^{125}$I-AcLDL to haSR-BI in transiently transfected COS cells (greater than 50% inhibition at concentrations greater than 10 μg/phospholipid/ml), while PC had virtually no effect at concentrations as high as 250 μg phospholipid/ml. Similar results are shown for cells transfected with huCD36 in FIG. 7B. The extent of PS inhibition of $^{125}$I-LDL binding depended on the relative PS content of the liposomes. FIG. 7C shows that inhibition by 500 μg phospholipid/ml increased substantially as the amount of PS in PS/PC mixed liposomes increased from 0 to 50 mol % of total phospholipid, with greater than 50% inhibition occurring when the PS mol % was greater than 10. These competition experiments suggest that anionic phospholipids bound to haSR-BI at a site close to or identical with the site of native and modified LDL binding and that polyvalent binding via multiple anionic phospholipid molecules may be involved.

The specific recognition of anionic phospholipids in the outer leaflets of cell membranes and lipoproteins by cell surface receptors may play an important role in a variety of physiologic and pathophysiologic process, including recognition of damaged or senescent cells by the reticuloendothelial system or lipoprotein hemeostasis. These studies support the role of SR-BI in these interactions.

Tissue Distribution of haSR-BI

To explore the physiological functions of haSR-BI, the tissue distribution of haSR-BI was determined in murine tissues and during differentiation of 3T3-L1 cells into adipocytes using Northern blot. Each lane was loaded with 0.5 µg of poly(A)+ RNA prepared from the murine tissues: kidney, liver, brain, testis, fat, diaphragm, heart, lung, spleen, or from 3T3-L1 fibroblasts which were either non-confluent at the fibroblast stage or confluent and induced to differentiate over a period of 0, 2, 4, 6 or 8 days. The blots were hybridized with a 600 base pair fragment of the coding region of haSR-BI. Hsp70 cDNA was used as a control for equal RNA loading. In the Northern of the murine tissues, the same blot was used for both SR-BI and hsp70 hybridizations. In the Northern of the differentiating 3T3-L1 cells, parallel blots were used. The blot of the murine tissues was also hybridized with a CD36 probe demonstrating that CD36 and SR-BI probes recognized different mRNA species.

One predominant band of approximately 2.4 kb was most abundant in fat and was present at moderate levels in lung and liver. There was little expression in the remaining tissues tested, which included kidney, brain, testis, diaphragm, heart, and spleen. To further investigate the expression of SR-BI in fat, the SR-BI mRNA levels in 3T3-L1 cells which were induced to differentiate into adipocytes were determined. The levels of SR-BI mRNA were found to increase during differentiation in a manner similar to that previously demonstrated for the glucose transporter GLUT4 and for Rab3D, a small molecular weight GTP binding protein (Baldini et al., 1992). These data, together with the data showing that modified LDL binding is inhibited by LDL, indicate that SR-BI plays a physiological role in lipid metabolism in adipocytes. In this regard, it is noteworthy that rat CD36 (also known as the "FAT" protein) was cloned as a result of its ability to directly bind reactive fatty acid esters (Abumrad et al., 1993). CD36 message is also markedly increased upon differentiation of the cultured lines 3T3 F442A and Ob1771 into adipocytes, as is the message for SR-BI in the 3T3-L1 adipocyte system. The expression patterns of SR-BI mRNA and CD36 mRNA are similar, but not identical. Both are found in high levels in adipose tissue. One notable difference in expression levels is found in the liver, where SR-BI expression is moderate but no CD36 message was detected. The observation that native LDL competes for AcLDL binding to SR-BI further indicated that SR-BI may play a role in lipid metabolism.

In contrast to the studies detecting mRNA encoding SR-BI, blots using polyclonal antibodies to a cytoplasmic region of SR-BI found that very high levels of protein were present in liver, adrenal tissues, and ovary in mice and rats, but only very low or undetectable levels in either white or brown fat, muscle or a variety of other tissues. Bands in the rat tissues were present at approximately 80 to 95 kD in liver but a smaller molecular weight protein of approximately 57 to 69 kD was detected in the steroidogenic tissues, including adrenal tissues and testes. This indicates that the mRNA present in the adipose or steroidogenic tissue actually encodes a close relative of SR-BI, rather than SR-BI, that the SR-BI mRNa is not translated into protein in fat in rodents, and/or that there may be alternative splicing of the SR-BI gene. In the mouse tissues, only the 80 to 95 kD form was observed in the liver and steroidogenic tissues. This is the same form observed in transfected cultured cells.

Recycling of HDL and Lipid Uptake Studies

Figure 8B:
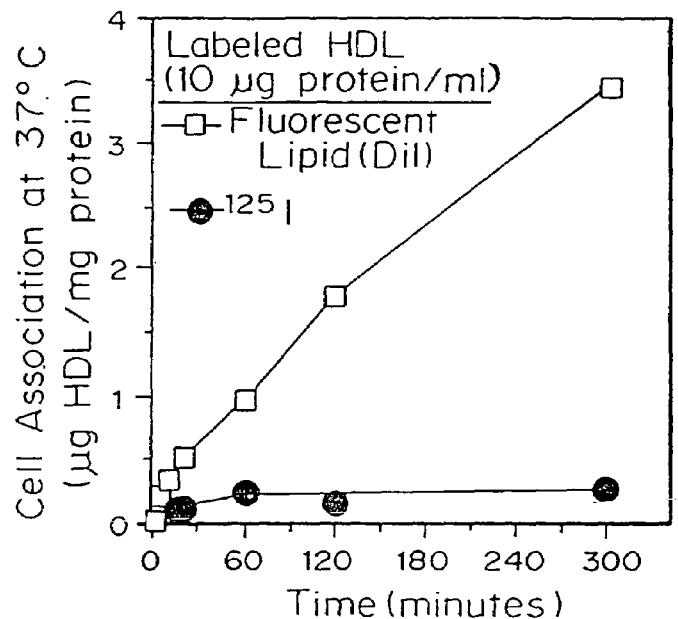
FIG. 8B is a graph of SR-BI mediated delivery of fluorescent lipid from HDL to cells expressing SR-BI on their surface, cell association at 37° C. (µg HDL/mg protein) as a function of time (minutes), for fluorescent lipid-labeled HDL (squares) and $^{125}$I-labeled HDL (circles).

It is significant that SR-BI binds HDL and is present in high levels in the liver and in tissues which are known to take up cholesterol from HDL for use in synthesis of steroids. Further studies were conducted to determine if the HDL bound to cells expressing SR-BI is recycled, i.e., if lipid bound to the HDL is taken up by the cell over time while the amount of HDL remains relatively constant. This is demonstrated in FIG. 8B. It is evident that the amount of HDL bound by the cells, as measured using $^{125}$I-labeled HDL, remains relatively constant after a steady state condition is reached thirty minutes to an hour after addition of the HDL to the cells. In contrast, the amount of fluorescent lipid in the cells continues to increase over time, demonstrating that the HDL must be binding the cells, not being internalized or degraded, and that the lipid bound to the HDL being internalized and retained within the cells. The results with DiI are predictive of results with cholesterol ester. Controls with untransfected cells, in which there was no binding to the cells or fluorescent lipid transfer, are evidence that this is a receptor dependent function.

Figure 9:
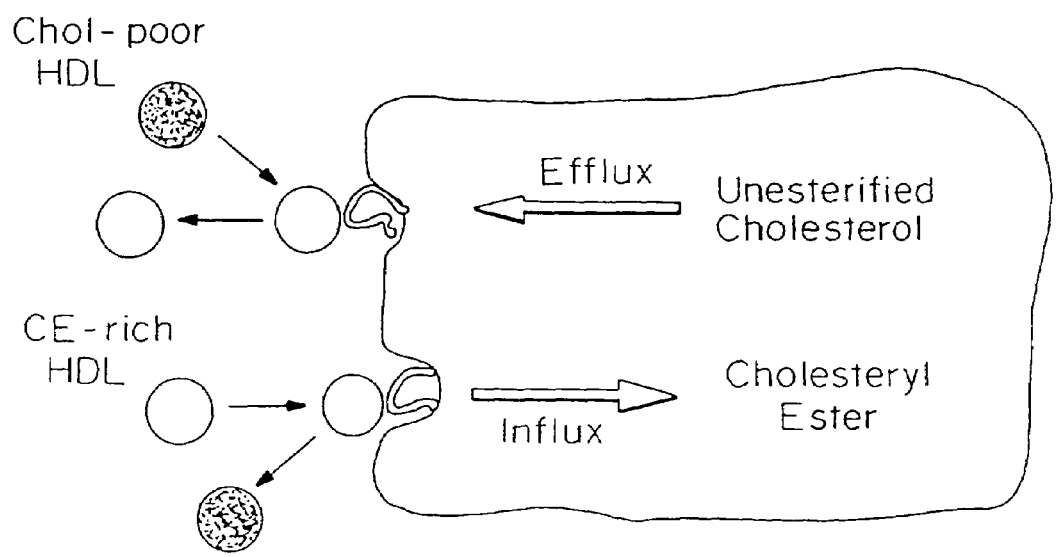
FIG. 9 is a schematic of potential roles of SR-BI in HDL metabolism.

The possible roles of SR-BI in HDL metabolism is shown schematically in FIG. 9. It is extremely likely that SR-BI and the related SR-B proteins play critical roles in HDL mediated lipid metabolism and transport. SR-BI appears to be responsible for cholesterol delivery to steroidogenic tissues and liver. It would be useful to increase expression of SR-BI in cells in which uptake of cholesterol can be increased, freeing HDL to serve as a means for removal of cholesterol from storage cells such as foam cells where it can play a role in atherogenesis.

II. *Drosophila melanogaster* Scavenger Receptor Protein

In an effort to further define the structures and functions of scavenger receptors, receptor expression was investigated in a representative invertebrate, *Drosophila melanogaster* (Abrams, et al. 1993 *Proc. Natl. Acad. USA* 89:10375–10379). By examining *D. melanogaster* embryos using fluorescently labeled AcLDL and $^{125}$I-AcLDL as probes for receptor activity in vivo and in vitro, fluorescence was found to be distributed throughout the interstitial spaces of the body cavity in a pattern characteristic of the distribution of embryonic macrophages and was observed in cells with multivesicular inclusions characteristic of macrophages. Further analysis of primary embryonic cell cultures showed that uptake was macrophage specific and exhibited the broad specificity of mammalian scavenger receptors.

Two commonly used *Drosophila* cell lines were examined for scavenger receptor activity: L2 and Kc. Only the Schneider L2 cells, not the Kc cells, exhibit a scavenger receptor-mediated endocytic pathway, which is almost identical to that of mammalian macrophages. The L2 cell receptors exhibit characteristic scavenger receptor-like broad polyanion-binding specificity, and mediate high-affinity and saturable binding, uptake and degradation of AcLDL. In L2 cells, the kinetics of intracellular ligand degradation after binding and uptake shows a lag phase, intracellular ligand degradation is chloroquine sensitive, and endocytosis is temperature dependent.

Preparation of cDNA and Genomic Libraries:

To facilitate both hybridization and expression cloning, cDNA libraries were generated from poly A+ RNA from L2 cells using standard procedures, as described above for Var-261 cells, and libraries were generated in the expression vector pcDNA1 (Invitrogen). The average insert size for the bidirectional L2 cell library is about 1.4 kb. DNAs for hybridization and transfection experiments were prepared as follows: *E. coli* strain MC1061/P3 is transformed with the cDNA expression library by electroporation and the transformed cells plated on LB-A/T plates (LB with Amp (15 μg/ml)/Tet (8 μg/ml)) to obtain isolated colonies at densities of 2,000 to 10,000 per 150 mm dish. Each plate, representing one pool, is scraped to recover the bacteria and a pool of library plasmids is isolated from each dish of bacteria using a midiprep method (miniprep method of Sambrook et al., 198, Molecular Cloning: A Laboratory Manual. Cold Spring Harbor Laboratory Press, Cold Spring Harbor, N.Y., scaled up five to ten fold). The pools can be used for Southern blot analysis for hybridization screening and for transfection into COS or CHO cells for expression cloning.

Expression in Cultured Mammalian Cells.

Expression of the receptors can be detected using either or both fluorescence microscopy and light microscopy of emulsion autoradiographs. Transient expression can be routinely obtained in COS cells, stable expression in CHO cells.

Fluorescence screening: Scavenger receptor activity can be detected using fluorescent, 1,1'-dioctadecyl-3,3,3',3'-tetramethylindocarbocyanine perchlorate-labeled AcLDL (DiI-AcLDL). On day 0, COS M6 cells are plated in 35 mm culture dishes (3 to 4×10$^5$ cells/dish) in medium A (DMEM supplemented with 100 units penicillin/ml medium, 100 μg streptomycin/ml medium, and 2 mM glutamine) containing 10% FBS (medium B). On day 1, the cells are transfected with 0.5 μg/dish of library DNA following the method of Cullen, 1987 *Methods in Enz.* 152:684–704. On day 2, monolayers were re-fed with modified medium B 1 mM sodium butyrate. On day 3, the monolayers are re-fed with modified medium B containing between one and five μg protein/ml of DiI-AcLDL. After a 5 hr incubation at 37° C., the plates are washed two times with PBS and the cells fixed with 3.7% formaldehyde in PBS for 10 min at room temperature. The presence of fluorescent DiI in the fixed cells is determined by visual screening using a Lietz inverted fluorescence microscope.

After screening the bidirectional L2 cell library, a pool of approximately 3500 clones which reproducibly conferred DiI-AcLDL endocytic activity in transiently transfected COS cells was identified. This pool was subdivided into 18 subpools of approximately 350 clones each, which were transfected into COS cells. One of these subpools also conferred DiI-AcLDL endocytic activity.

The clone from the subpool was isolated and transfected into CHO cells to yield CHO[dSR-CI]-2.6a cells. The nucleic acid (Sequence ID No. 5) and amino acid (Sequence ID No. 6) sequences were also obtained using the methods described above.

Binding Activity of CHO[dSR-CI]-2.6a Cells

Binding of $^{125}$I-AcLDL to CHO[dSR-CI]-2.6a cells was measured as ng AcLDL protein bound/mg cell protein at concentrations of 1, 3, 6, 13, 25, and 50 μg AcLDL protein/ml. Uptake was also measured, comparing total, nonspecific and specific binding.

Figure 6A:
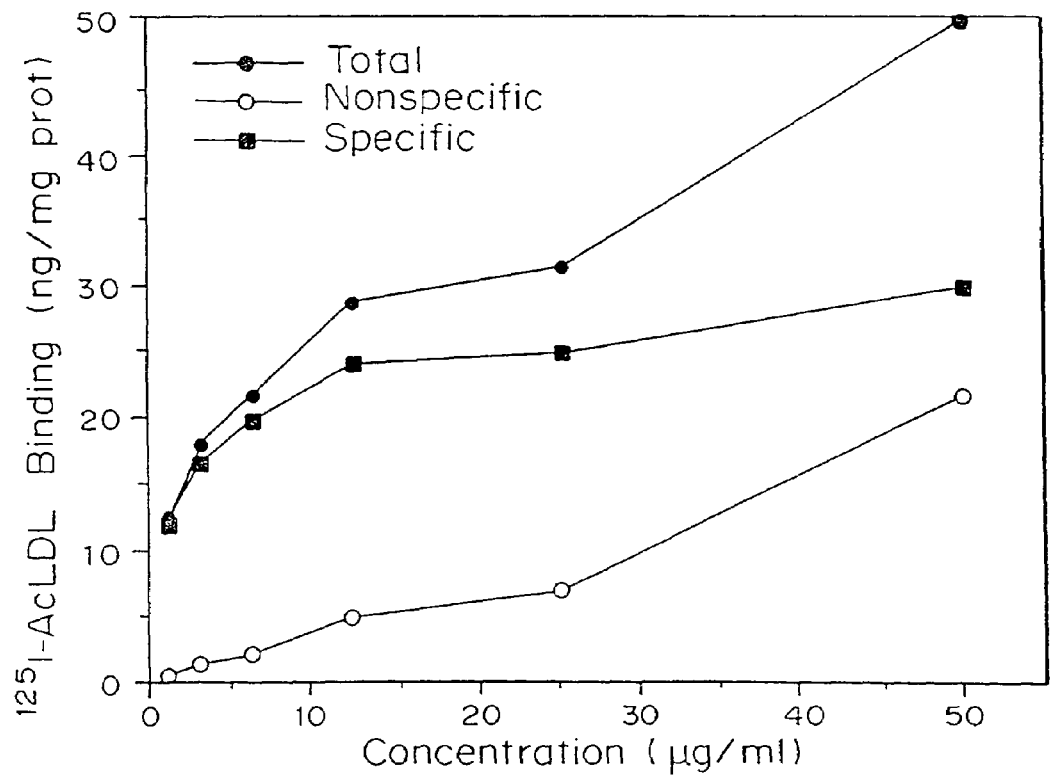
FIGS. 6A, 6B, and 6C are graphs of the concentration dependent binding, uptake and degradation of $^{125}$I-AcLDL to CHO[dSR-CI]-2.6a cells.
Figure 6B:
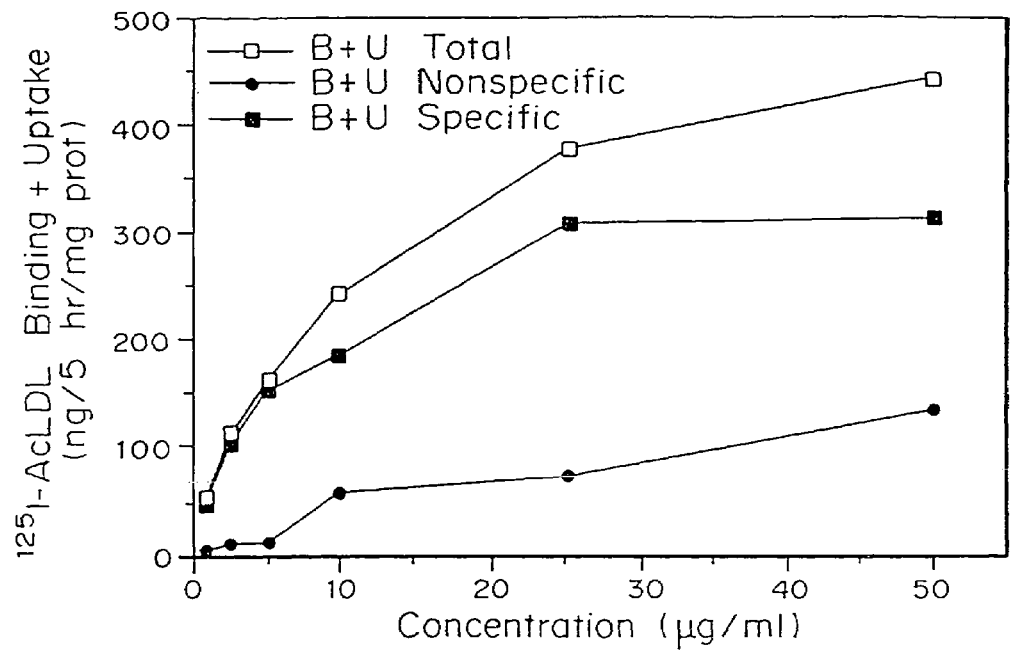

As shown by FIG. 6A, dSR-CI binds AcLDL. As shown by FIG. 6B, AcLDL was also taken up by the cells expressing dSR-CI.

Figure 6C:
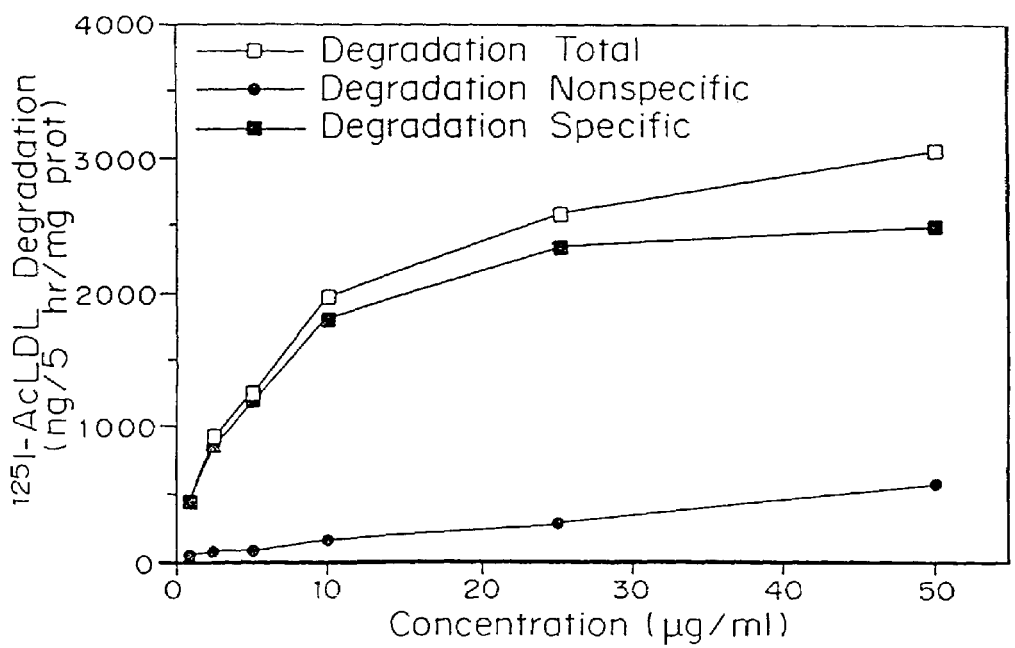

Degradation was measured to confirm that dSR-CI mediated internalization of the AcLDL. The results shown in FIG. 6C confirm the selective degradation of AcLDL.

Competitive binding of AcLDL was performed to more accurately define the specificity of the AcLDL binding. The results are shown below in Table 1.

TABLE 1

Competitive Inhibition of $^{125}$I-AcLDL Degradation Activity by CHO [dSR-CI]-2.6a Cells.

| Competitor | Degradation (% No Competitor) |
| --- | --- |
| None | 100 |
| AcLDL (400 μg/ml) | 4.8 |
| LDL (400 μg/ml) | 97.6 |
| M-BSA (400 μg/ml) | 6.7 |
| BSA (400 μg/ml) | 94.4 |
| poly I (400 μg/ml) | 2.7 |
| dA5G37 (100 μg/ml) | 5.1 |
| dA37 (100 μg/ml) | 98.2 |
| dA37 (400 μg/ml) | 43.0 |
| Dextran Sulfate | 4.2 |
| Dextran (400 μg/ml) | 100 |
| Poly D-glutamic acid (400 μg/ml) | 34 |

III. Applications of the Scavenger Receptor Proteins

The presence of scavenger receptors on both mammalian and *Drosophila* macrophages suggests that they mediate critical, well-conserved functions, possibly pathogen recognition, and raises the possibility that they may have appeared early in the evolution of host defense systems. In this regard, it is known that postembryonic macrophage-like hemocytes in *Drosophila* participate in wound healing, encapsulation of pathogens, and phagocytosis. Furthermore, macrophages play an important role in the recognition of apoptotic or senescent cells during the course of development, normal cell turnover, and aging, although it is not known if the scavenger receptors are also involved in these processes. The binding specificity of the SR-BI protein implicates this receptor in additional or alternative roles critical to HDL metabolism and the delivery of cholesterol to steroidogenic tissues.

Accordingly, the understanding of the structure and functions of the receptor proteins described herein, as well as the cDNAs encoding these proteins, have a variety of uses. Specifically, the proteins and their DNAs can be used in screening of drugs which modulate the activity and/or the expression of the receptors; in screening of patient samples for the presence of functional receptor protein; in the case of the SR-BI receptor protein, removal of LDL, modified LDL, VLDL, or HDL by reaction with immobilized receptor protein; use of the DNA to construct probes for screening of libraries for other receptors, including the human equivalents, and the regulatory sequences controlling the expression of the other receptors as well as SR-BI and SR-CI. These drugs, when identified, may be useful in treating or preventing atherosclerosis, fat uptake by adipocytes, and some types of immune disorders.

Isolation of Other Receptor Proteins.

Figure 1B:
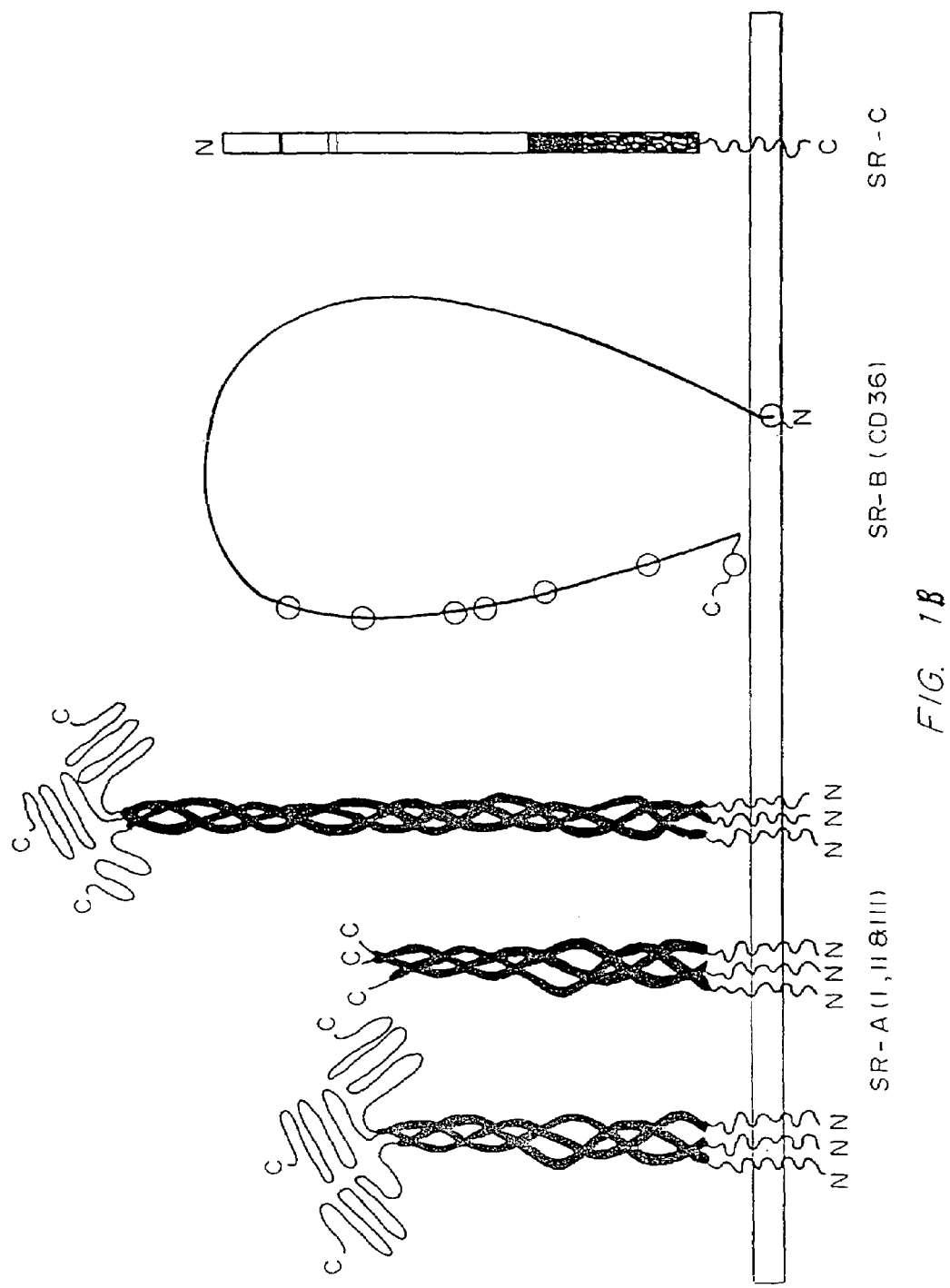
FIG. 1*b* is a schematic of the three classes of scavenger receptors, SR-A (I, II and III), SR-B (CD36), and SR-C.

The nucleotide sequences identified herein as encoding hamster SR-BI and *Drosophila melanogaster* SR-CI are useful as probes for screening of libraries for the presence of related receptors. Libraries are constructed from cells of a desired species, such as humans, which are then screened with all or a portion of the nucleotide sequence encoding either SR-BI or SR-CI. Specific regions of interest are those portions of the nucleotide sequence which encode regions of the protein conserved between different receptors; between the same receptors from different species; and within discrete regions of the receptor proteins: the cytoplasmic region, the transmembrane region, the "stem" regions that may include EGF repeats, collagen like regions α-helical coiled regions, or regions having a high density of cysteines (CCP domains), and specific ligand regions. These regions are identified by structural analysis such as that which has been used to generate the schematics in FIGS. 1A and 1B, using methods routinely available to those skilled in the art. These methods include chemical crosslinking, electrophoretic analysis, hydrodynamic studies, and electron microscopy and computer assisted analysis of structure based on predicted amino acid sequence.

As used herein, unless specifically stated otherwise, the term "SR-BI" refers to the nucleotide and amino acid sequences, respectively, shown in Sequence ID Nos. 3 and 4, and 7 and 8, and degenerate variants thereof and their equivalents in other species of origin, especially human, as well as functionally equivalent variants, having additions, deletions, and substitutions of either nucleotides or amino acids which do not significantly alter the functional activity of the protein as a receptor characterized by the binding activity identified above. The term "SR-CI" refers to the sequences shown in Sequence ID Nos. 5 and 6, and degenerate variants thereof and their equivalents in other species of origin, especially human, as well as functionally equivalent variants, having additions, deletions, and substitutions of either nucleotides or amino acids which do not significantly alter the functional activity of the protein as a receptor characterized by the binding activity identified above.

Preferred uses for these sequences, especially those in the Sequence Listings below, are for the cloning of equivalent receptor molecules present in human cells, for the isolation and characterization of the regulatory sequences present in the genome which controlled the extent to which a particular receptor is expressed in a cell, and for the screening of drugs altering binding of or endocytosis of ligand by the scavenger receptor proteins.

Isolation of Receptor Proteins

Additional receptor proteins for study can be obtained by expression in suitable recombinant host systems, such as mammalian, yeast, bacteria, or insect cells. Isolation can be facilitated by making antibodies to the recombinant protein which are then immobilized on substrates for use in purification of additional receptors.

As discussed above with regard to tissue distribution, it appears that at least one different but closely related protein is encoded by a nucleotide sequence present in steroidogenic tissues in rodents which hybridizes to Sequence ID No. 3 under stringent conditions, and can be isolated using routine techniques and the materials described herein.

Screening of Patient Samples for Expression of Receptor Proteins.

The sequences disclosed herein are useful in screening of patient samples for the presence of normal receptor proteins, using hybridization assays of patient samples, including blood and tissues. Screening can also be accomplished using antibodies, typically labeled with a fluorescent, radiolabeled, or enzymatic label, or by isolation of target cells and screening for binding activity, as described in the examples above. Typically, one would be screening for expression on either a qualitative or quantitative basis, and for expression of functional receptor.

Hybridization Probes

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. In general, the longer the sequence or higher the G and C content, the higher the temperature and/or salt concentration required. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Generation of Antibodies for Diagnostic or Therapeutic Use

Antibodies to the receptor proteins can also be generated which are useful in detection, characterization or isolation of receptor proteins, as well as for modifying receptor protein activity, in most cases, through inhibition of binding. Antibodies are generated by standard techniques, using human or animal receptor proteins. Since the proteins exhibit high evolutionary conservation, it may be advantageous to generate antibodies to a protein of a different species of origin than the species in which the antibodies are to be tested or utilized, looking for those antibodies which are immunoreactive with the most evolutionarily conserved regions. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., 1991 *Nucl. Acids Res.*, 19:2471–2476, incorporated herein by reference, may be used. Briefly, the variable region DNA of a selected animal recombinant anti-idiotypic ScFv is sequenced by the method of Clackson, T., et al., 1991 *Nature*, 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals).

Screening for Drugs Modifying or Altering the Extent of Receptor Function or Expression The receptor proteins are useful as targets for compounds which turn on, or off, or otherwise regulate binding to these receptors. The assays described above clearly provide routine methodology by which a compound can be tested for an inhibitory effect on binding of a specific compound, such as a radiolabeled modified LDL or polyion. The in vitro studies of compounds which appear to inhibit binding selectively to the receptors are then confirmed by animal testing. Since the molecules are so highly evolutionarily conserved, it is possible to conduct studies in laboratory animals such as mice to predict the effects in humans.

Studies based on inhibition of binding are predictive for indirect effects of alteration of receptor binding. For example, inhibition of LDL binding to the SR-BI receptor leads to decreased uptake by cells of LDL and therefore decreases deposition of LDL in cells; similar effects should be observed for inhibition of lipoprotein and/or lipid by adipocytes expressing the SR-BI receptor. Conversely, increasing LDL binding to cells increases removal of lipids from the blood stream and thereby decreases lipid deposition within the blood stream. Studies have been conducted using a stimulator to enhance macrophage uptake of cholesterol and thereby treat atherogenesis, using M-CSF (Schaub, et al., 1994 *Arterioscler. Thromb.* 14(1), 70–76; Inaba, et al., 1993 *J. Clin. Invest.* 92(2), 750–757). Although the target of the stimulator is not known with specificity, this provides further support for the rationale for believing the indirect in vivo effects can be achieved based on the in vitro binding data.

Studies described above and the results shown in FIG. 8 demonstrate that drugs increasing expression of SR-BI or closely related proteins in tissues such as liver would be useful in enhancing removal of cholesterol from the circulation and foam cells.

Assays for testing compounds for useful activity can be based solely on interaction with the receptor protein, preferably expressed on the surface of transfected cells such as those described above, although proteins in solution or immobilized on inert substrates can also be utilized, where the indication is inhibition or increase in binding of LDL or modified LDL.

Alternatively, the assays can be based on interaction with the gene sequence encoding the receptor protein, preferably the regulatory sequences directing expression of the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor activity in transfected or naturally occurring cells which express the receptor, then in vivo in laboratory animals. Typically, the antisense would inhibit expression. However, sequences which block those sequences which "turn off" synthesis can also be targeted.

The receptor protein for study can be isolated from either naturally occurring cells or cells which have been genetically engineered to express the receptor, as described in the examples above. In the preferred embodiment, the cells would have been engineered using the intact gene.

Random Generation of Receptor or Receptor Encoding Sequence Binding Molecules.

Molecules with a given function, catalytic or ligand-binding, can be selected for from a complex mixture of random molecules in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, *QSAR: Quantitative Structure-Activity Relationships in Drug Design* pp. 189–193 (Alan R. Liss, Inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Generation of Nucleic Acid Regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, 1993 *Science*, 260, 926–932; U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., 1993 *Science* 261, 209–211; incorporated herein by reference).

The 5' flanking sequences of the receptor gene can also be used to inhibit the expression of the receptor. For example, an antisense RNA of all or a portion of the 5' flanking region of the receptor gene can be used to inhibit expression of the receptor in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the receptor gene can be inserted into an appropriate expression vector so that upon passage into the cell, the transcription of the inserted DNA yields an antisense RNA that is complementary to the mRNA transcript of the receptor protein gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the receptor protein gene to ensure that the antisense RNA contains complementary sequences present on the mRNA. Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci.,* 83, 4143–4146; Wickstrom et al., 1988 *Proc. Natl. Acad. Sci. USA* 85, 1028–1032; Crooke, 1993 *FASEB J.* 7, 533–539. Furthermore, recent work has shown that improved inhibition of expression of a gene by antisense oligonucleotides is possible if the antisense oligonucleotides contain modified nucleotides (see, e.g., Offensperger et. al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725–730; Orson et al., 1991 *Nucl. Acids Res.* 19, 3435–3441; Postal et al., 1991 *Proc. Natl. Acad. Sci. USA* 88, 8227–8231; Cooney et al., 1988 *Science* 241, 456–459; Young et al., 1991 *Proc. Natl. Acad. Sci. USA* 88, 10023–10026; Duval-Valentin et al., 1992 *Proc. Natl. Acad. Sci. USA* 89, 504–508; 1992 Blume et al., *Nucl. Acids Res.* 20, 1777–1784; 1992 Grigoriev et al., *J. Biol. Chem.* 267, 3389–3395.

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 *Mol. Cell. Biol.* 8, 963–973; Wickstrom et al., 1988 *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620 (1980) (phosphotriester method). Accordingly, DNA sequences of the 5' flanking region of the receptor protein gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a receptor protein gene in order to inhibit expression of the gene.

In some cases it may be advantageous to insert enhancers or multiple copies of the regulatory sequences into an expression system to facilitate screening of methods and reagents for manipulation of expression.

Preparation of Receptor Protein Fragments

Compounds which are effective for blocking binding of the receptor can also consist of fragments of the receptor proteins, expressed recombinantly and cleaved by enzymatic digest or expressed from a sequence encoding a peptide of less than the full length receptor protein. These will typically be soluble proteins, i.e., not including the transmembrane and cytoplasmic regions, although smaller portions determined in the assays described above to inhibit or compete for binding to the receptor proteins can also be utilized. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking receptor binding, the $IC_{50}$, the dose of peptide required to inhibit binding by 50%, ranges from about 50 µM to about 300 µM, depending on the peptides. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of the receptor proteins, or, preferably, by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 µg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered.

Pharmaceutical Compositions

Compounds which alter receptor protein binding are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

Removal of LDL from Patients or Patient Samples

The SR-BI receptor proteins can be used to remove LDL from patient blood, by immobilizing the receptor on a suitable substrate, such as the cellulose membrane of a dialysis unit, using conventional coupling, for example, using carboimide. The patient's blood is then dialyzed through the unit.

Modifications and variations of the methods and materials described herein will be obvious to those skilled in the art and are intended to be encompassed by the following claims. The teachings of the references cited herein are specifically incorporated herein.

We claim:

1. An isolated nucleic acid molecule encoding a scavenger receptor protein type BI which selectively binds to low density lipoprotein and to modified lipoprotein having the characteristics of acetylated low density lipoprotein in cell medium containing 10% serum, wherein the binding of acetylated low density lipoprotein to the scavenger receptor protein type BI is inhibited by native low density lipoprotein, and the isolated nucleic molecule hybridizes to SEQ ID Nos. 3 and 7 under moderately stringent hybridization conditions at a temperature of approximately 25° C. below the melting temperature of a perfectly base-paired double-stranded DNA molecule consisting of SEQ ID NO:3 or 7.

2. The molecule of claim 1 expressed in cells selected from the group consisting of adipocytes, lung cells and liver cells.

3. The molecule of claim 1 hybridizing under stringent hybridization conditions at a temperature greater than 25° C. below the melting temperature of a perfectly base-paired double-stranded DNA to a molecule with Sequence ID No. 3.

4. An isolated nucleic acid molecule encoding a scavenger receptor protein having the sequence of Sequence ID No. 3.

5. An isolated nucleic acid molecule encoding a protein with the amino acid sequence shown in Sequence ID No. 4.

6. The molecule of claim 1 which encodes a human scavenger receptor.

7. The molecule of claim 1 labeled with a detectable label.

8. An expression vector comprising the molecule of claim 1 encoding the scavenger receptor protein.

9. A host cell comprising the nucleic acid molecule of claim 1.

10. A method for screening for a compound which alters the binding of scavenger receptor protein type BI comprising providing an assay for binding of low density lipoprotein or modified low density lipoprotein to the scavenger receptor protein, adding the compound to be tested to the assay, and determining if the amount of modified low density lipoprotein or low density lipoprotein which is bound to the scavenger receptor protein is altered as compared to binding in the absence of the compound to be tested.

11. The method of claim 10 wherein the assay includes a cell expressing the scavenger receptor protein and the compound is a nucleic acid molecule which alters expression of the scavenger receptor protein.

12. The method of claim 10 wherein the compound is selected from a library of compounds which are randomly tested for alteration of binding.

13. The method of claim 10 wherein the compound competitively inhibits binding of low density lipoprotein or modified lipoprotein having the characteristics of acetylated low density lipoprotein to the scavenger receptor protein.

14. A method for removing low density lipoprotein from patient blood comprising reacting the blood with immobilized scavenger receptor protein type B, wherein the scavenger receptor protein type BI is encoded by a nucleotide molecule hybridizing to SEQ ID Nos. 3 and 7 under moderately stringent hybridization conditions at a temperature of approximately 25° C. below the melting temperature of a perfectly base-paired double-stranded DNA molecule consisting of SEQ ID NO:3 or 7 and selectively binds to low density lipoprotein and to modified lipoprotein having the characteristics of acetylated low density lipoprotein in cell medium containing 10% serum, under conditions wherein the low density lipoprotein is bound to the scavenger receptor, wherein the binding of acetylated low density lipoprotein to the scavenger receptor protein type BI is inhibited by native low density lipoprotein.

15. A method for inhibiting uptake of lipoprotein or lipids by adipocytes comprising administering a compound selectively inhibiting binding of lipoprotein to the scavenger receptor protein type BI, wherein the scavenger receptor protein type BI is encoded by a nucleotide molecule hybridizing to SEQ ID Nos. 3 and 7 under moderately stringent hybridization conditions at a temperature of approximately 25° C. below the melting temperature of a perfectly base-paired double-stranded DNA molecule consisting of SEQ ID NO:3 or 7 and selectively binds to low density lipoprotein and to modified lipoprotein having the characteristics of acetylated low density lipoprotein, under conditions wherein the low density lipoprotein is bound to the scavenger receptor wherein the binding of acetylated low density lipoprotein to the scavenger receptor protein type BI is inhibited by native low density lipoprotein.

16. A method for screening patients for abnormal scavenger receptor protein activity or function comprising determining the presence of scavenger receptor protein type BI, and comparing the scavenger receptor for to determine if the quantity present or the function of the receptor is equivalent to that present normal cells.

* * * * *

UNITED STATES PATENT AND TRADEMARK OFFICE
CERTIFICATE OF CORRECTION

PATENT NO. : 7,078,511 B1
APPLICATION NO. : 08/765108
DATED : July 18, 2006
INVENTOR(S) : Monty Krieger and Susan L. Acton It is certified that error appears in the above-identified patent and that said Letters Patent is hereby corrected as shown below:

Claim 10, column 52 and 53, lines 58 through 2, replace claim 10 with --A method for screening for a compound which alters the binding of scavenger receptor protein type BI, which is encoded by a nucleotide molecule hybridizing to SEQ ID Nos. 3 and 7 under moderately stringent hybridization conditions at a temperature of approximately 25°C below the melting temperature of a perfectly base-paired double-stranded DNA molecule consisting of SEQ ID NO:3 or 7 and which selectively binds to low density lipoprotein and to modified lipoprotein having the characteristics of acetylated low density lipoprotein in cell medium containing 10% serum, wherein the binding of acetylated low density lipoprotein to the scavenger receptor protein type BI is inhibited by native low density lipoprotein, comprising providing reagents for use in an assay for binding of low density lipoprotein or modified low density lipoprotein to the scavenger receptor protein the reagents comprising SR-BI, low density lipoprotein or modified low density lipoprotein, and means for determining if the low density lipoprotein or modified low density lipoprotein is bound to the scavenger receptor protein, adding the compound to be tested to the assay, and determining if the amount of modified low density lipoprotein or low density lipoprotein which is bound to the scavenger receptor protein is altered as compared to binding in the absence of the compound to be tested.--

Claim 16, column 54, lines 21 through 27, replace claim 16 with --A method for screening patients for abnormal scavenger receptor protein activity or function comprising determining the presence of scavenger receptor protein type BI, wherein the scavenger receptor protein type BI is encoded by a nucleotide molecule hybridizing to SEQ ID Nos. 3 and 7 under moderately stringent hybridization conditions at a temperature of approximately 25°C below the melting temperature of a perfectly base-paired double-stranded DNA molecule consisting of SEQ ID NO:3 or 7 and selectively binds to low density lipoprotein and to modified lipoprotein having the characteristics of acetylated low density lipoprotein, wherein the binding of acetylated low density lipoprotein to the scavenger receptor protein type BI is inhibited by native low density lipoprotein, and Signed and Sealed this
Eleventh Day of October, 2011

David J. Kappos
*Director of the United States Patent and Trademark Office*

CERTIFICATE OF CORRECTION (continued)
U.S. Pat. No. 7,078,511 B1 determining if the quantity present or the function of the receptor is equivalent to that present in normal cells.--

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (x) PUBLICATION INFORMATION:
      (A) AUTHORS: Ashkenas, et al.
      (C) JOURNAL: J. Lipid Res.
      (D) VOLUME: 34
      (F) PAGES: 983-1000
      (G) DATE: 1993
      (K) RELEVANT RESIDUES IN SEQ ID NO:1: FROM 1 TO 20

(xi) SEQUENCE DESCRIPTION: SEQ ID NO:1:

AATGAAGAAC TGCTTAGTTT          20

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (x) PUBLICATION INFORMATION:
      (A) AUTHORS: Ashkenas, et al.
      (C) JOURNAL: J. Lipid Res.
      (D) VOLUME: 34
      (F) PAGES: 983-1000
      (G) DATE: 1993
      (K) RELEVANT RESIDUES IN SEQ ID NO:1: FROM 1 TO 18

(xi) SEQUENCE DESCRIPTION: SEQ ID NO:2:

AATCAAGGAA TTTAACTG          18

(2) INFORMATION FOR SEQ ID NO:3:

(i) SEQUENCE CHARACTERISTICS:
        (A) LENGTH: 1788 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 156..1683
        (D) OTHER INFORMATION: /function= "Nucleotides 156 through
            1683 encode the amino acid sequence for the Hamster
            Scavenger Receptor Class B-I."

(xi) SEQUENCE DESCRIPTION: SEQ ID NO:3:

```
GCCACCTGCA GGGCTACTGC TGCTCCGGCC ACTGCCTGAG ACTCACCTTG CTGGAACGTG      60
AGCCTCGGCT TCTGTCATCT CTGTGGCCTC TGTCGCTTCT GTCGCTGTCC CCCTTCAGTC     120
CCTGAGCCCC GCGAGCCCGG GCCGCACACG CGGACATGGG CGGCAGCGCC AGGGCGCGCT     180
GGGTGGCGGT GGGGCTGGGC GTCGTGGGGC TGCTGTGCGC TGTGCTCGGT GTGGTTATGA     240
TCCTCGTGAT GCCCTCGCTC ATCAAACAGC AGGTACTGAA GAATGTCCGC ATAGACCCCA     300
GCAGCCTGTC CTTTGCAATG TGGAAGGAGA TCCCTGTACC CTTCTACTTG TCCGTCTACT     360
TCTTCGAGGT GGTCAATCCC AGCGAGATCC TAAAGGGTGA GAAGCCAGTA GTGCGGGAGC     420
GTGGACCCTA TGTCTACAGG GAATTCAGAC ATAAGGCCAA CATCACCTTC AATGACAATG     480
ATACTGTGTC CTTTGTGGAG CACCGCAGCC TCCATTTCCA GCCGGACAGG TCCCACGGCT     540
CTGAGAGTGA CTACATTATA CTGCCTAACA TTCTGGTCTT GGGGGGCGCA GTAATGATGG     600
AGAGCAAGTC TGCAGGCCTG AAGCTGATGA TGACCTTGGG GCTGGCCACC TTGGGCCAGC     660
GTGCCTTTAT GAACCGAACA GTTGGTGAGA TCCTGTGGGG CTATGAGGAT CCCTTCGTGA     720
ATTTTATCAA CAAATACTTA CCAGACATGT CCCCATCAA GGGCAAGTTC GGCCTGTTTG     780
TTGAGATGAA CAACTCAGAC TCTGGGCTCT TCACTGTGTT CACGGGCGTC CAGAACTTCA     840
GCAAGATCCA CCTGGTGGAC AGATGGAATG GGCTCAGCAA GGTCAACTAC TGGCATTCAG     900
AGCAGTGCAA CATGATCAAT GGCACTTCCG GGCAGATGTG GCACCATTC ATGACACCCC     960
AGTCCTCGCT GGAATTCTTC AGTCCGGAAG CCTGCAGGTC TATGAAGCTC ACCTACCATG    1020
ATTCAGGGGT GTTTGAAGGC ATCCCCACCT ATCGCTTCAC AGCCCCTAAA ACTTTGTTTG    1080
CCAATGGGTC TGTTTACCCA CCCAATGAAG GTTTCTGCCC GTGCCTTGAA TCCGGCATTC    1140
AAAATGTCAG CACTTGCAGG TTTGGTGCAC CCCTGTTTCT GTCACACCCT CACTTCTACA    1200
ATGCAGACCC TGTGCTATCA GAAGCCGTTC TGGGTCTGAA CCCTGACCCA AGGGAGCATT    1260
CTTTGTTCCT TGACATCCAT CCGGTCACTG GGATCCCCAT GAACTGTTCT GTGAAGTTGC    1320
AGATAAGCCT CTACATCAAA GCTGTCAAGG GCATTGGGCA AACAGGGAAG ATCGAGCCCG    1380
TGGTCCTCCC ATTGCTGTGG TTTGAGCAGA GCGGTGCCAT GGGCGGCGAG CCCCTGAACA    1440
CGTTCTACAC GCAGCTGGTG CTGATGCCCC AGGTACTTCA GTATGTGCAG TATGTGCTGC    1500
TGGGGCTGGG CGGCCTCCTG CTGCTGGTGC CCGTCATCTA CCAGTTGCGC AGCCAGGAGA    1560
AATGCTTTTT ATTTTGGAGT GGTAGTAAAA AGGGCTCGCA GGATAAGGAG GCCATTCAGG    1620
CCTACTCTGA GTCTCTGATG TCACCAGCTG CCAAGGGCAC GGTGCTGCAA GAAGCCAAGC    1680
```

```
TGTAGGGTCC CAAAGACACC ACGAGCCCCC CCAACCTGAT AGCTTGGTCA GACCAGCCAT      1740

CCAGCCCCTA CACCCCGCTT CTTGAGGACT CTCTCAGCGG ACAGTCGC                   1788
```

(2) INFORMATION FOR SEQ ID NO:4:

(i) SEQUENCE CHARACTERISTICS:
      (A) LENGTH: 509 amino acids
      (B) TYPE: amino acid
      (D) TOPOLOGY: linear (ii) MOLECULE TYPE: protein (iii) HYPOTHETICAL: NO (v) FRAGMENT TYPE: internal (ix) FEATURE:
      (A) NAME/KEY: misc_feature
      (B) LOCATION: 1..509
      (D) OTHER INFORMATION: /function= "Amino acid sequence for the
          Hamster Scavenger Receptor Class B-I."

(ix) FEATURE:
      (A) NAME/KEY: Domain
      (B) LOCATION: 9..32
      (D) OTHER INFORMATION: /note= "Putative transmembrane
          domain."

(ix) FEATURE:
      (A) NAME/KEY: Domain
      (B) LOCATION: 440..464
      (D) OTHER INFORMATION: /note= "Putative transmembrane
          domain."

(ix) FEATURE:
      (A) NAME/KEY: Modified-site
      (B) LOCATION: 1..385
      (D) OTHER INFORMATION: /note= "Positions 102-104, 108-110,
      (D) OTHER INFORMATION: 173-175, 212-214, 227-229, 255-257,
      (D) OTHER INFORMATION: 310-312, 330-332 and 383-385 represent
      (D) OTHER INFORMATION: potential N-linked glycosylation
          sites."

(ix) FEATURE:
      (A) NAME/KEY: Modified-site
      (B) LOCATION: 21..470
      (D) OTHER INFORMATION: /note= "The cysteines at positions
          21, 251, 280, 321, 323, 334, 384 and 470 represent
          potential disulfide linkages."

(xi) SEQUENCE DESCRIPTION: SEQ ID NO:4:

```
Met Gly Gly Ser Ala Arg Ala Arg Trp Val Ala Val Gly Leu Gly Val
1               5                   10                  15

Val Gly Leu Leu Cys Ala Val Leu Gly Val Val Met Ile Leu Val Met
            20                  25                  30

Pro Ser Leu Ile Lys Gln Gln Val Leu Lys Asn Val Arg Ile Asp Pro
        35                  40                  45

Ser Ser Leu Ser Phe Ala Met Trp Lys Glu Ile Pro Val Pro Phe Tyr
    50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
            100                 105                 110

Phe Val Glu His Arg Ser Leu His Phe Gln Pro Asp Arg Ser His Gly
        115                 120                 125
```

```
Ser Glu Ser Asp Tyr Ile Ile Leu Pro Asn Ile Leu Val Leu Gly Gly
    130                 135                 140

Ala Val Met Met Glu Ser Lys Ser Ala Gly Leu Lys Leu Met Met Thr
145                 150                 155                 160

Leu Gly Leu Ala Thr Leu Gly Gln Arg Ala Phe Met Asn Arg Thr Val
                165                 170                 175

Gly Glu Ile Leu Trp Gly Tyr Glu Asp Pro Phe Val Asn Phe Ile Asn
                180                 185                 190

Lys Tyr Leu Pro Asp Met Phe Pro Ile Lys Gly Lys Phe Gly Leu Phe
                195                 200                 205

Val Glu Met Asn Asn Ser Asp Ser Gly Leu Phe Thr Val Phe Thr Gly
    210                 215                 220

Val Gln Asn Phe Ser Lys Ile His Leu Val Asp Arg Trp Asn Gly Leu
225                 230                 235                 240

Ser Lys Val Asn Tyr Trp His Ser Glu Gln Cys Asn Met Ile Asn Gly
                245                 250                 255

Thr Ser Gly Gln Met Trp Ala Pro Phe Met Thr Pro Gln Ser Ser Leu
                260                 265                 270

Glu Phe Phe Ser Pro Glu Ala Cys Arg Ser Met Lys Leu Thr Tyr His
    275                 280                 285

Asp Ser Gly Val Phe Glu Gly Ile Pro Thr Tyr Arg Phe Thr Ala Pro
    290                 295                 300

Lys Thr Leu Phe Ala Asn Gly Ser Val Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Gly Ala Pro Leu Phe Leu Ser His Pro His Phe Tyr Asn Ala Asp Pro
                340                 345                 350

Val Leu Ser Glu Ala Val Leu Gly Leu Asn Pro Asp Pro Arg Glu His
    355                 360                 365

Ser Leu Phe Leu Asp Ile His Pro Val Thr Gly Ile Pro Met Asn Cys
370                 375                 380

Ser Val Lys Leu Gln Ile Ser Leu Tyr Ile Lys Ala Val Lys Gly Ile
385                 390                 395                 400

Gly Gln Thr Gly Lys Ile Glu Pro Val Val Leu Pro Leu Leu Trp Phe
                405                 410                 415

Glu Gln Ser Gly Ala Met Gly Gly Glu Pro Leu Asn Thr Phe Tyr Thr
                420                 425                 430

Gln Leu Val Leu Met Pro Gln Val Leu Gln Tyr Val Gln Tyr Val Leu
            435                 440                 445

Leu Gly Leu Gly Gly Leu Leu Leu Leu Val Pro Val Ile Tyr Gln Leu
            450                 455                 460

Arg Ser Gln Glu Lys Cys Phe Leu Phe Trp Ser Gly Ser Lys Lys Gly
465                 470                 475                 480

Ser Gln Asp Lys Glu Ala Ile Gln Ala Tyr Ser Glu Ser Leu Met Ser
                485                 490                 495

Pro Ala Ala Lys Gly Thr Val Leu Gln Glu Ala Lys Leu
                500                 505
```

-continued (2) INFORMATION FOR SEQ ID NO:5:

(i) SEQUENCE CHARACTERISTICS:
        (A) LENGTH: 2032 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc. feature
        (B) LOCATION: 40..1926
        (D) OTHER INFORMATION:   /Function = "Nucleotides 40 through
        (D) OTHER INFORMATION:   1926 encode the amino acid sequence
        (D) OTHER INFORMATION:   for the Drosophila Melanogaster
        (D) OTHER INFORMATION:   Scavenger Receptor Class CI."

(xi) SEQUENCE DESCRIPTION: SEQ ID NO:5:

```
GACCGTATCT ATACATTAAG TTCGTAATAT CTCTGCGGAA TGGAATTTTT CTGGACTCTG      60

GCTGTGATTG TGATATATTG TATAGGTCAC ATTCATGGAC GATGTGAAAG ATCTATAGAT     120

TTGGATAATG GAAGTATAAA TTATCGACAG AGAAATATAG TGAGATTCAG ATGCAATCGC     180

GGCTACACTT TGCAGGGAAC AGTAATGCAA ACTTGCGATC GAGATGGTCG CCTTCGAGGC     240

GAAAAACCAT TCTGTGCCAG TAGGGGATGT GCGAGGCCCG AGGATCCGGA GAACGGACAC     300

GTCGAAAATC TTTCCCTAAG GGCGGATGTC GTGTGCCACG ATGGCTATGT CTTGGTCGGT     360

GGTCGCACTG CCTACTGCGA TGGAGAAAGA TGGAGCACCC AGCTGGGATC GTGTCGAAGG     420

AGCAACCACA CAAGAGATCA TTCTTGCGAT TTCGAGAGCG AGGATCAGTG CGGTTGGGAG     480

GCGGAGACAA CCTTCCGACG ACCCTGGAAG CGAGTCAGCA CGGTATCCGA TATTCACTCC     540

CTAAGAACGG GACCCCGCCA CGATCACACG TTTAAAAACG AATCCGGTGG TCATTACATG     600

CGCATGGAAA CCCAAATGGG GGCTTATGGA AGCTACCATC TGCTATCGCC GATCTATCCC     660

AGATCCCTCA CCCTGAAGAC CGCCTGCTGC TTTCGATTCC ACTACTTCAT GTTTGGCGCT     720

GGTGTGGATA ATCTGGTGGT GTCCGTTAAA CCCGTTTCGA TGCCAATGGC AACCATGTGG     780

AATAGGTTCA GAGCCAATTG CAGCAAATTT GAGATATCTG GTCAGCAGGG AACCCAGTGG     840

CTAGAGCACA CGATCAGCAT TGACGAGATG CAAGAGGACT TCCAGGTGAT ATTCACGGCA     900

ACGGATGCAA GATCCCAATT CGGAGATATT GCCATCGATG ATGTAAAGCT AATGACAGGC     960

AGTGAGTGTG GCACAAACGG ATTTAGCACC ACCACAGAAC CAACGGCTCC GACAGGCAGC    1020

AACGAGCAAC CACTGGTCTA CGATATGATA AGTTGTTCAG GTCGATGCGG AACATCAATG    1080

TCGGCCTCCA ATATAACCAA CAATGGTATA GTCATGGGAT GTGGATGTAA TGACGAGTGC    1140

CTTTCGGATG AGACTTGTTG CCTAAACTAT TTGGAGGAGT GCACAAAGGA GCTGCTCACC    1200

ACGACCGAGG ATGATATTAG TTCCCTGCCC CCAACGGTCA CATCAACAAG CACAAGCACT    1260

ACGAGGAAGT CAACAACAAC AACAACCACA AGCACGACTA CTACAAGTAC AACAACAACT    1320

AAAAGGCCAA CCACAACCAC AACAACAACA AAGGCCACAA CTACAAAGCG AACAACAACC    1380

ACTAAAAAAC CGACAACAAC TTCAACAACG CCGAAGCCAA CAACAACGAC TTCAACCACA    1440

CCAAAGTCTA CAACTTCTAC AACGTCTACA ACTTCAACAA CACCAACGAC AACAACTACA    1500

ATAAATGTGT TTACAACAAA GAAAACAACA ATAATGATCC CTACTTCCAG TACCGAAAAG    1560

ACTACAGGCA TCATCACCAC CATGAAGACA CGCAAGCGCA TCACTTGGAA CGTTGATCCT    1620

CAGGACATCG AGGGTCACAT GGACACGAGC GGAAGTACCC CCAATCCAGC TTTAGTAGTA    1680
```

```
CTTTACCTGC TACTCGGCAT TGTTCTGGTG GTAGTTCTGG CCAACGTCGT TAATCGCTGG      1740

ATAATACCAA TCACTGGATC AAAGACCAGC AGCGAAAAGG CTGTGAGATT CAAGAAGGCA      1800

TTCGATAGTC TGAAGAAGCA ACGGAAAAGA AACAGCATGG ATGATCAGCC GTTATGCGAC      1860

TCCGATAACG ACGATGTAGA GTATTTCGAA GAAATGGGCG TGGACATACG ACATAGGACC      1920

GATCTATGAG GGTAATCCCC AGTGATACCA AAACAAACGC TTAGGCCTGT GCCTATTGTA      1980

TAGGATGTTT CTAAATGTGT ATGCAAGAAT CGAATAAAAG AAAATATGCA AC             2032

(2) INFORMATION FOR SEQ ID NO:6:

(i) SEQUENCE CHARACTERISTICS:
        (A) LENGTH: 629 amino acids
        (B) TYPE: amino acid
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: misc. feature
        (B) LOCATION: 1..629
        (D) OTHER INFORMATION:  /Function = "Amino acid sequence for
            the Drosophila Melanogaster Scavenger Receptor Class CI."

(ix) FEATURE:
        (A) NAME/KEY: Modified-site
        (B) LOCATION: 30..353
        (D) OTHER INFORMATION: /note= "Positions 30-32, 90-92,
            129-131, 180-182, 253-255 and 351-353 represent
            potential N-glycosylation sites."

(ix) FEATURE:
        (A) NAME/KEY: Modified-site
        (B) LOCATION: 1..20
        (D) OTHER INFORMATION: /note= "Amino acids 1-20 represent
            a putative signal sequence."

(ix) FEATURE:
        (A) NAME/KEY: Modified-site
        (B) LOCATION: 21..74
        (D) OTHER INFORMATION: /note= "Amino acids 21-74 represent
            complement control protein domain
            number 1."

(ix) FEATURE:
        (A) NAME/KEY: Modified-site
        (B) LOCATION: 75..127
        (D) OTHER INFORMATION: /note= "Amino acids 75-127
            represent complement control protein
            domain number 2."

(ix) FEATURE:
        (A) NAME/KEY: Modified-site
        (B) LOCATION: 128..312
        (D) OTHER INFORMATION: /note= "Amino acids 128-312
            represent an MAM domain."

(ix) FEATURE:
        (A) NAME/KEY: Disulfide-bond
        (B) LOCATION: 22..381
        (D) OTHER INFORMATION: /note= "The cysteines at positions
        (D) OTHER INFORMATION: 22, 45, 59, 72, 77, 99, 113, 125,
        (D) OTHER INFORMATION: 136, 144, 216, 217, 254, 310, 339, 343,
        (D) OTHER INFORMATION: 361, 363, 367, 373, 374 and 381
                              represent
        (D) OTHER INFORMATION: potential disulfide linkages."
```

(ix) FEATURE:
            (A) NAME/KEY: Modified-site
            (B) LOCATION: 338..381
            (D) OTHER INFORMATION: /note= "Amino acids 338-381
                represent a somatomedin B domain."

(ix) FEATURE:
            (A) NAME/KEY: Modified-site
            (B) LOCATION: 387..514
            (D) OTHER INFORMATION: /note= "Amino acids 387-514
                represent a mucin-like potential
                O-linked glycosylation region."

(ix) FEATURE:
            (A) NAME/KEY: Domain
            (B) LOCATION: 544..564
            (D) OTHER INFORMATION: /note= "Amino acids 544-565
                represent a putative TM domain."

(ix) FEATURE:
            (A) NAME/KEY: Domain
            (B) LOCATION: 565..629
            (D) OTHER INFORMATION: /note= "Amino acids 565-629
                represent a putative cytoplasmic
                domain."

(ix) FEATURE:
            (A) NAME/KEY: Modified-site
            (B) LOCATION: 576..602
            (D) OTHER INFORMATION: /note= "Amino acids 576-579 and
                599-602 represent casein kinase II
                sites."

(ix) FEATURE:
            (A) NAME/KEY: Modified-site
            (B) LOCATION: 578..592
            (D) OTHER INFORMATION: /note= "Amino acids 578-580 and
                590-592 represent protein kinase C
                sites."

(ix) FEATURE:
            (A) NAME/KEY: Modified-site
            (B) LOCATION: 596..599
            (D) OTHER INFORMATION: /note= "Amino acids 596-599
                represent a cAMP protein kinase site."

(xi) SEQUENCE DESCRIPTION: SEQ ID NO:6:

Met Glu Phe Phe Trp Thr Leu Ala Val Ile Val Ile Tyr Cys Ile Gly
 1               5                  10                  15

His Ile His Gly Arg Cys Glu Arg Ser Ile Asp Leu Asp Asn Gly Ser
            20                  25                  30

Ile Asn Tyr Arg Gln Arg Asn Ile Val Arg Phe Arg Cys Asn Arg Gly
        35                  40                  45

Tyr Thr Leu Gln Gly Thr Val Met Gln Thr Cys Asp Arg Asp Gly Arg
 50                  55                  60

Leu Arg Gly Glu Lys Pro Phe Cys Ala Ser Arg Gly Cys Ala Arg Pro
65                  70                  75                  80

Glu Asp Pro Glu Asn Gly His Val Glu Asn Leu Ser Leu Arg Ala Asp
                85                  90                  95

Val Val Cys His Asp Gly Tyr Val Leu Val Gly Gly Arg Thr Ala Tyr
            100                 105                 110

Cys Asp Gly Glu Arg Trp Ser Thr Gln Leu Gly Ser Cys Arg Arg Ser
        115                 120                 125

Asn His Thr Arg Asp His Ser Cys Asp Phe Glu Ser Glu Asp Gln Cys
130                 135                 140

Gly Trp Glu Ala Glu Thr Thr Phe Arg Arg Pro Trp Lys Arg Val Ser
145                 150                 155                 160

-continued

```
Thr Val Ser Asp Ile His Ser Leu Arg Thr Gly Pro Arg His Asp His
                165                 170                 175
Thr Phe Lys Asn Glu Ser Gly Gly His Tyr Met Arg Met Glu Thr Gln
                180                 185                 190
Met Gly Ala Tyr Gly Ser Tyr His Leu Leu Ser Pro Ile Tyr Pro Arg
                195                 200                 205
Ser Leu Thr Leu Lys Thr Ala Cys Cys Phe Arg Phe His Tyr Phe Met
            210                 215                 220
Phe Gly Ala Gly Val Asp Asn Leu Val Val Ser Val Lys Pro Val Ser
225                 230                 235                 240
Met Pro Met Ala Thr Met Trp Asn Arg Phe Arg Ala Asn Cys Ser Lys
                245                 250                 255
Phe Glu Ile Ser Gly Gln Gln Gly Thr Gln Trp Leu Glu His Thr Ile
                260                 265                 270
Ser Ile Asp Glu Met Gln Glu Asp Phe Gln Val Ile Phe Thr Ala Thr
            275                 280                 285
Asp Ala Arg Ser Gln Phe Gly Asp Ile Ala Ile Asp Asp Val Lys Leu
            290                 295                 300
Met Thr Gly Ser Glu Cys Gly Thr Asn Gly Phe Ser Thr Thr Thr Glu
305                 310                 315                 320
Pro Thr Ala Pro Thr Gly Ser Asn Glu Gln Pro Leu Val Tyr Asp Met
                325                 330                 335
Ile Ser Cys Ser Gly Arg Cys Gly Thr Ser Met Ser Ala Ser Asn Ile
                340                 345                 350
Thr Asn Asn Gly Ile Val Met Gly Cys Gly Cys Asn Asp Glu Cys Leu
            355                 360                 365
Ser Asp Glu Thr Cys Cys Leu Asn Tyr Leu Glu Glu Cys Thr Lys Glu
            370                 375                 380
Leu Leu Thr Thr Thr Glu Asp Asp Ile Ser Ser Leu Pro Pro Thr Val
385                 390                 395                 400
Thr Ser Thr Ser Thr Ser Thr Thr Arg Lys Ser Thr Thr Thr Thr Thr
                405                 410                 415
Thr Ser Thr Thr Thr Thr Ser Thr Thr Thr Lys Arg Pro Thr Thr Thr
                420                 425                 430
Thr Thr Thr Thr Lys Ala Thr Thr Thr Lys Arg Thr Thr Thr Thr Thr
            435                 440                 445
Lys Lys Pro Thr Thr Thr Ser Thr Thr Pro Lys Pro Thr Thr Thr Thr
450                 455                 460
Ser Thr Thr Pro Lys Ser Thr Thr Ser Thr Thr Ser Thr Thr Ser Thr
465                 470                 475                 480
Thr Pro Thr Thr Thr Thr Thr Ile Asn Val Phe Thr Thr Lys Lys Thr
                485                 490                 495
Thr Ile Met Ile Pro Thr Ser Ser Thr Glu Lys Thr Thr Gly Ile Ile
            500                 505                 510
Thr Thr Met Lys Thr Arg Lys Arg Ile Thr Trp Asn Val Asp Pro Gln
            515                 520                 525
Asp Ile Glu Gly His Met Asp Thr Ser Gly Ser Thr Pro Asn Pro Ala
            530                 535                 540
Leu Val Val Leu Tyr Leu Leu Gly Ile Val Leu Val Val Val Val Leu
545                 550                 555                 560
Ala Asn Val Val Asn Arg Trp Ile Ile Pro Ile Thr Gly Ser Lys Thr
                565                 570                 575
```

```
Ser Ser Glu Lys Ala Val Arg Phe Lys Lys Ala Phe Asp Ser Leu Lys
            580                 585                 590

Lys Gln Arg Lys Arg Asn Ser Met Asp Asp Gln Pro Leu Cys Asp Ser
        595                 600                 605

Asp Asn Asp Asp Val Glu Tyr Phe Glu Glu Met Gly Val Asp Ile Arg
    610                 615                 620

His Arg Thr Asp Leu
625

(2) INFORMATION FOR SEQ ID NO:7:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 51..1577
        (D) OTHER INFORMATION:  /Function = "Nucleotides 51 through
            1577 encode the amino acid sequence for the murine
            Scavenger Receptor Class BI."

(xi) SEQUENCE DESCRIPTION: SEQ ID NO:7:

CCGTCTCCTT CAGGTCCTGA GCCCCGAGAG CCCCTTCCGC GCACGCGGAC ATG GGC         56
                                                      Met Gly
                                                        1

GGC AGC TCC AGG GCG CGC TGG GTG GCC TTG GGG TTG GGC GCC CTG GGG      104
Gly Ser Ser Arg Ala Arg Trp Val Ala Leu Gly Leu Gly Ala Leu Gly
        5                   10                  15

CTG CTG TTT GCT GCG CTC GGC GTT GTC ATG ATC CTC ATG GTG CCC TCC      152
Leu Leu Phe Ala Ala Leu Gly Val Val Met Ile Leu Met Val Pro Ser
        20                  25                  30

CTC ATC AAG CAG CAG GTG CTC AAG AAT GTC CGC ATA GAC CCG AGC AGC      200
Leu Ile Lys Gln Gln Val Leu Lys Asn Val Arg Ile Asp Pro Ser Ser
 35                 40                  45                  50

CTG TCC TTC GGG ATG TGG AAG GAG ATC CCC GTC CCT TTC TAC TTG TCT      248
Leu Ser Phe Gly Met Trp Lys Glu Ile Pro Val Pro Phe Tyr Leu Ser
            55                  60                  65

GTC TAC TTC TTC GAA GTG GTC AAC CCA AAC GAG GTC CTC AAC GGC CAG      296
Val Tyr Phe Phe Glu Val Val Asn Pro Asn Glu Val Leu Asn Gly Gln
        70                  75                  80

AAG CCA GTA GTC CGG GAG CGT GGA CCC TAT GTC TAC AGG GAG TTC AGA      344
Lys Pro Val Val Arg Glu Arg Gly Pro Tyr Val Tyr Arg Glu Phe Arg
    85                  90                  95

CAA AAG GTC AAC ATC ACC TTC AAT GAC AAC GAC ACC GTG TCC TTC GTG      392
Gln Lys Val Asn Ile Thr Phe Asn Asp Asn Asp Thr Val Ser Phe Val
100                 105                 110

GAG AAC CGC AGC CTC CAT TTC CAG CCT GAC AAG TCG CAT GGC TCA GAG      440
Glu Asn Arg Ser Leu His Phe Gln Pro Asp Lys Ser His Gly Ser Glu
115                 120                 125                 130

AGT GAC TAC ATT GTA CTG CCT AAC ATC TTG GTC CTG GGG GGC TCG ATA      488
Ser Asp Tyr Ile Val Leu Pro Asn Ile Leu Val Leu Gly Gly Ser Ile
                135                 140                 145

TTG ATG GAG AGC AAG CCT GTG AGC CTG AAG CTG ATG ATG ACC TTG GCG      536
Leu Met Glu Ser Lys Pro Val Ser Leu Lys Leu Met Met Thr Leu Ala
            150                 155                 160
```

```
                                                              -continued

CTG GTC ACC ATG GGC CAG CGT GCT TTT ATG AAC CGC ACA GTT GGT GAG        584
Leu Val Thr Met Gly Gln Arg Ala Phe Met Asn Arg Thr Val Gly Glu
            165                 170                 175

ATC CTG TGG GGC TAT GAC GAT CCC TTC GTG CAT TTT CTC AAC ACG TAC        632
Ile Leu Trp Gly Tyr Asp Asp Pro Phe Val His Phe Leu Asn Thr Tyr
        180                 185                 190

CTC CCA GAC ATG CTT CCC ATA AAG GGC AAA TTT GGC CTG TTT GTT GGG        680
Leu Pro Asp Met Leu Pro Ile Lys Gly Lys Phe Gly Leu Phe Val Gly
195                 200                 205                 210

ATG AAC AAC TCG AAT TCT GGG GTC TTC ACT GTC TTC ACG GGC GTC CAG        728
Met Asn Asn Ser Asn Ser Gly Val Phe Thr Val Phe Thr Gly Val Gln
                215                 220                 225

AAT TTC AGC AGG ATC CAT CTG GTG GAC AAA TGG AAC GGA CTC AGC AAG        776
Asn Phe Ser Arg Ile His Leu Val Asp Lys Trp Asn Gly Leu Ser Lys
            230                 235                 240

ATC GAT TAT TGG CAT TCA GAG CAG TGT AAC ATG ATC AAT GGG ACT TCC        824
Ile Asp Tyr Trp His Ser Glu Gln Cys Asn Met Ile Asn Gly Thr Ser
        245                 250                 255

GGG CAG ATG TGG GCA CCC TTC ATG ACA CCC GAA TCC TCG CTG GAA TTC        872
Gly Gln Met Trp Ala Pro Phe Met Thr Pro Glu Ser Ser Leu Glu Phe
260                 265                 270

TTC AGC CCG GAG GCA TGC AGG TCC ATG AAG CTG ACC TAC AAC GAA TCA        920
Phe Ser Pro Glu Ala Cys Arg Ser Met Lys Leu Thr Tyr Asn Glu Ser
275                 280                 285                 290

AGG GTG TTT GAA GGC ATT CCC ACG TAT CGC TTC ACG GCC CCC GAT ACT        968
Arg Val Phe Glu Gly Ile Pro Thr Tyr Arg Phe Thr Ala Pro Asp Thr
                295                 300                 305

CTG TTT GCC AAC GGG TCC GTC TAC CCA CCC AAC GAA GGC TTC TGC CCA       1016
Leu Phe Ala Asn Gly Ser Val Tyr Pro Pro Asn Glu Gly Phe Cys Pro
            310                 315                 320

TGC CGA GAG TCT GGC ATT CAG AAT GTC AGC ACC TGC AGG TTT GGT GCG       1064
Cys Arg Glu Ser Gly Ile Gln Asn Val Ser Thr Cys Arg Phe Gly Ala
        325                 330                 335

CCT CTG TTT CTC TCC CAC CCC CAC TTT TAC AAC GCC GAC CCT GTG TTG       1112
Pro Leu Phe Leu Ser His Pro His Phe Tyr Asn Ala Asp Pro Val Leu
340                 345                 350

TCA GAA GCT GTT CTT GGT CTG AAC CCT AAC CCA AAG GAG CAT TCC TTG       1160
Ser Glu Ala Val Leu Gly Leu Asn Pro Asn Pro Lys Glu His Ser Leu
355                 360                 365                 370

TTC CTA GAC ATC CAT CCG GTC ACT GGG ATC CCC ATG AAC TGT TCT GTG       1208
Phe Leu Asp Ile His Pro Val Thr Gly Ile Pro Met Asn Cys Ser Val
                375                 380                 385

AAG ATG CAG CTG AGC CTC TAC ATC AAA TCT GTC AAG GGC ATC GGG CAA       1256
Lys Met Gln Leu Ser Leu Tyr Ile Lys Ser Val Lys Gly Ile Gly Gln
            390                 395                 400

ACA GGG AAG ATC GAG CCA GTA GTT CTG CCG TTG CTG TGG TTC GAA CAG       1304
Thr Gly Lys Ile Glu Pro Val Val Leu Pro Leu Leu Trp Phe Glu Gln
        405                 410                 415

AGC GGA GCA ATG GGT GGC AAG CCC CTG AGC ACG TTC TAC ACG CAG CTG       1352
Ser Gly Ala Met Gly Gly Lys Pro Leu Ser Thr Phe Tyr Thr Gln Leu
420                 425                 430

GTG CTG ATG CCC CAG GTT CTT CAC TAC GCG CAG TAT GTG CTG CTG GGG       1400
Val Leu Met Pro Gln Val Leu His Tyr Ala Gln Tyr Val Leu Leu Gly
435                 440                 445                 450

CTT GGA GGC CTC CTG TTG CTG GTG CCC ATC ATC TGC CAA CTG CGC AGC       1448
Leu Gly Gly Leu Leu Leu Val Pro Ile Ile Cys Gln Leu Arg Ser
                455                 460                 465

CAG GAG AAA TGC TTT TTG TTT TGG AGT GGT AGT AAA AAG GGC TCC CAG       1496
Gln Glu Lys Cys Phe Leu Phe Trp Ser Gly Ser Lys Lys Gly Ser Gln
            470                 475                 480
```

-continued

```
GAT AAG GAG GCC ATT CAG GCC TAC TCT GAG TCC CTG ATG TCA CCA GCT      1544
Asp Lys Glu Ala Ile Gln Ala Tyr Ser Glu Ser Leu Met Ser Pro Ala
            485                 490                 495

GCC AAG GGC ACG GTG CTG CAA GAA GCC AAG CTA TAGGGTCCTG AAGACACTAT    1597
Ala Lys Gly Thr Val Leu Gln Glu Ala Lys Leu
    500                 505

AAGCCCCCCA AACCTGATAG CTTGGTCAGA CCAGCCACCC AGTCCCTACA CCCCGCTTCT    1657

TGAGGACTCT CTCAGCGGAC AGCCCACCAG TGCCATGGCC TGAGCCCCCA GATGTCACAC    1717

CTGTCCGCAC GCACGGCACA TGGATGCCCA CGCATGTGCA AAAACAACTC AGGGACCAGG    1777

GACAGACC                                                             1785
```

(2) INFORMATION FOR SEQ ID NO:8:

(i) SEQUENCE CHARACTERISTICS:
        (A) LENGTH: 509 amino acids
        (B) TYPE: amino acid
        (D) TOPOLOGY: linear (ii) MOLECULE TYPE: protein (ix) FEATURE:
        (A) NAME/KEY: misc. feature
        (B) LOCATION: 1..509
        (D) OTHER INFORMATION: /Function = "Amino acid sequence for
            the murine Scavenger Receptor Class BI."

(xi) SEQUENCE DESCRIPTION: SEQ ID NO:8:

```
Met Gly Gly Ser Ser Arg Ala Arg Trp Val Ala Leu Gly Leu Gly Ala
 1               5                  10                  15

Leu Gly Leu Leu Phe Ala Ala Leu Gly Val Val Met Ile Leu Met Val
                20                  25                  30

Pro Ser Leu Ile Lys Gln Gln Val Leu Lys Asn Val Arg Ile Asp Pro
            35                  40                  45

Ser Ser Leu Ser Phe Gly Met Trp Lys Glu Ile Pro Val Pro Phe Tyr
        50                  55                  60

Leu Ser Val Tyr Phe Phe Glu Val Val Asn Pro Asn Glu Val Leu Asn
 65                  70                  75                  80

Gly Gln Lys Pro Val Val Arg Glu Arg Gly Pro Tyr Val Tyr Arg Glu
                85                  90                  95

Phe Arg Gln Lys Val Asn Ile Thr Phe Asn Asp Asn Asp Thr Val Ser
            100                 105                 110

Phe Val Glu Asn Arg Ser Leu His Phe Gln Pro Asp Lys Ser His Gly
        115                 120                 125

Ser Glu Ser Asp Tyr Ile Val Leu Pro Asn Ile Leu Val Leu Gly Gly
    130                 135                 140

Ser Ile Leu Met Glu Ser Lys Pro Val Ser Leu Lys Leu Met Met Thr
145                 150                 155                 160

Leu Ala Leu Val Thr Met Gly Gln Arg Ala Phe Met Asn Arg Thr Val
                165                 170                 175

Gly Glu Ile Leu Trp Gly Tyr Asp Asp Pro Phe Val His Phe Leu Asn
            180                 185                 190

Thr Tyr Leu Pro Asp Met Leu Pro Ile Lys Gly Lys Phe Gly Leu Phe
        195                 200                 205

Val Gly Met Asn Asn Ser Asn Ser Gly Val Phe Thr Val Phe Thr Gly
    210                 215                 220

Val Gln Asn Phe Ser Arg Ile His Leu Val Asp Lys Trp Asn Gly Leu
225                 230                 235                 240
```

```
Ser Lys Ile Asp Tyr Trp His Ser Glu Gln Cys Asn Met Ile Asn Gly
            245                 250                 255

Thr Ser Gly Gln Met Trp Ala Pro Phe Met Thr Pro Glu Ser Ser Leu
            260                 265                 270

Glu Phe Phe Ser Pro Glu Ala Cys Arg Ser Met Lys Leu Thr Tyr Asn
            275                 280                 285

Glu Ser Arg Val Phe Glu Gly Ile Pro Thr Tyr Arg Phe Thr Ala Pro
    290                 295                 300

Asp Thr Leu Phe Ala Asn Gly Ser Val Tyr Pro Pro Asn Glu Gly Phe
305                 310                 315                 320

Cys Pro Cys Arg Glu Ser Gly Ile Gln Asn Val Ser Thr Cys Arg Phe
            325                 330                 335

Gly Ala Pro Leu Phe Leu Ser His Pro His Phe Tyr Asn Ala Asp Pro
            340                 345                 350

Val Leu Ser Glu Ala Val Leu Gly Leu Asn Pro Asn Pro Lys Glu His
            355                 360                 365

Ser Leu Phe Leu Asp Ile His Pro Val Thr Gly Ile Pro Met Asn Cys
    370                 375                 380

Ser Val Lys Met Gln Leu Ser Leu Tyr Ile Lys Ser Val Lys Gly Ile
385                 390                 395                 400

Gly Gln Thr Gly Lys Ile Glu Pro Val Val Leu Pro Leu Leu Trp Phe
            405                 410                 415

Glu Gln Ser Gly Ala Met Gly Gly Lys Pro Leu Ser Thr Phe Tyr Thr
            420                 425                 430

Gln Leu Val Leu Met Pro Gln Val Leu His Tyr Ala Gln Tyr Val Leu
            435                 440                 445

Leu Gly Leu Gly Gly Leu Leu Leu Leu Val Pro Ile Ile Cys Gln Leu
    450                 455                 460

Arg Ser Gln Glu Lys Cys Phe Leu Phe Trp Ser Gly Ser Lys Lys Gly
465                 470                 475                 480

Ser Gln Asp Lys Glu Ala Ile Gln Ala Tyr Ser Glu Ser Leu Met Ser
            485                 490                 495

Pro Ala Ala Lys Gly Thr Val Leu Gln Glu Ala Lys Leu
            500                 505
```